(12) United States Patent
Qian et al.

(10) Patent No.: US 7,271,167 B2
(45) Date of Patent: Sep. 18, 2007

(54) COMPOUNDS, COMPOSITIONS, AND METHODS

(75) Inventors: Xiangping Qian, South San Francisco, CA (US); Gustave Bergnes, South San Francisco, CA (US); David J. Morgans, Jr., South San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 0 days.

(21) Appl. No.: 10/529,630

(22) PCT Filed: Oct. 9, 2003

(86) PCT No.: PCT/US03/32318

§ 371 (c)(1),
(2), (4) Date: Jan. 31, 2006

(87) PCT Pub. No.: WO2004/032879

PCT Pub. Date: Apr. 22, 2004

(65) Prior Publication Data

US 2006/0173007 A1    Aug. 3, 2006

Related U.S. Application Data

(60) Provisional application No. 60/418,030, filed on Oct. 11, 2002.

(51) Int. Cl.
  *C07D 253/07* (2006.01)
  *C07D 403/06* (2006.01)
  *A61K 31/53* (2006.01)
  *A61P 35/00* (2006.01)

(52) U.S. Cl. .................................... 514/242; 544/182

(58) Field of Classification Search ................ 544/182; 514/242
See application file for complete search history.

(56) References Cited

U.S. PATENT DOCUMENTS 6,303,603 B1    10/2001    Patoiseau et al.

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition,vol. 1, 1004-1010, 1996.*
Haque et al. Cell Motility and Cytoskeleton, 58: 10-16, 2004.*
Yildiz et al., Trends in Cell Biology, 15(7):112-120, 2005.*
Maliga et al., Chem. Biol. 9(9): 989-996,2002.*
International Search Report mailed Jun. 10, 2004, for Application No. PCT/US03/32318, filed Oct. 9, 2003.
International Preliminary Examination Report mailed Jul. 16, 2004, for Application No. PCT/US03/32318, filed Oct. 9, 2003.

* cited by examiner

*Primary Examiner*—Venkataraman Balasubramanian
(74) *Attorney, Agent, or Firm*—Finnegan, Henderson, Farabow, Garrett & Dunner LLP

(57) ABSTRACT

1,2,4-Triazin-5-ones useful for treating cellular proliferative diseases and disorders by modulating the activity of KSP are disclosed.

23 Claims, No Drawings

US 7,271,167 B2

COMPOUNDS, COMPOSITIONS, AND METHODS

CROSS-REFERENCE TO RELATED PATENT APPLICATIONS

This application claims the benefit of U.S. Provisional Patent Application No. 60/418,030, filed Oct. 11, 2002; which is incorporated herein by reference for all purposes.

FIELD OF THE INVENTION

This invention relates to compounds which are inhibitors of the mitotic kinesin KSP and are useful in the treatment of cellular proliferative diseases, for example cancer, hyperplasias, restenosis, cardiac hypertrophy, immune disorders, fungal disorders, and inflammation.

BACKGROUND OF THE INVENTION

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the mitotic kinesins which have been identified is KSP. KSP belongs to an evolutionarily conserved kinesin subfamily of plus end-directed microtubule motors that assemble into bipolar homotetramers consisting of antiparallel homodimers. During mitosis KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described (Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J. Biol. Chem., 272:19418-24 (1997); Blangy, et al., Cell Motil Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426), and a fragment of the KSP gene (TRIP5) has been described (Lee, et al., Mol Endocrinol., 9:243-54 (1995); GenBank accession number L40372). *Xenopus* KSP homologs (Eg5), as well as *Drosophila* KLP61F/KRP1 30 have been reported.

Mitotic kinesins are attractive targets for the discovery and development of novel antimitotic chemotherapeutics. Accordingly, it is an object of the present invention to provide methods and compositions useful in the inhibition of KSP, a mitotic kinesin.

SUMMARY OF THE INVENTION

In accordance with the objects outlined above, the present invention provides compositions and methods that can be used to treat diseases of proliferating cells. The compositions are KSP inhibitors, particularly human KSP inhibitors.

In one aspect, the invention relates to methods for treating cellular proliferative diseases, for treating disorders by modulating the activity of KSP, and for inhibiting KSP kinesin. The methods employ one or more compounds represented by Formula I:

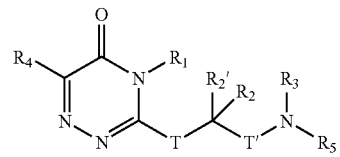

Formula I wherein:

T and T' are independently a covalent bond or optionally substituted lower alkylene;

$R_1$ is chosen from hydrogen, optionally substituted alkyl, optionally substituted aryl, optionally substituted aralkyl, optionally substituted heteroaryl, and optionally substituted heteroaralkyl;

$R_2$ and $R_{2'}$ are independently chosen from hydrogen, optionally substituted alkyl, optionally substituted aryl, optionally substituted aralkyl, optionally substituted heteroaryl, and optionally substituted heteroaralkyl; or $R_2$ and $R_{2'}$ taken together form an optionally substituted 3- to 7-membered ring;

$R_3$ is chosen from hydrogen, optionally substituted alkyl-, optionally substituted aryl-, optionally substituted aralkyl-, optionally substituted heteroaryl-, optionally substituted heteroaralkyl-, optionally substituted heterocyclyl, —C(O)—$R_6$, and —S(O)$_2$—$R_{6a}$;

$R_5$ is chosen from hydrogen, optionally substituted alkyl-, optionally substituted aryl-, optionally substituted aralkyl-, optionally substituted heteroaralkyl-, and optionally substituted heterocyclyl-;

$R_6$ is chosen from hydrogen, optionally substituted alkyl, optionally substituted aryl, optionally substituted aralkyl, optionally substituted heteroaryl, optionally substituted heteroaralkyl, $R_7O$— and $R_{12}$—NH—;

$R_{6a}$ is chosen from optionally substituted alkyl, optionally substituted aryl, optionally substituted aralkyl, optionally substituted heteroaryl, optionally substituted heteroaralkyl, and $R_{12}$—NH—;

or $R_5$ taken together with $R_3$, and the nitrogen to which they are bound, form an optionally substituted 5- to 12-membered nitrogen-containing heterocycle, which optionally incorporates from one to two additional heteroatoms, selected from N, O, and S in the heterocycle ring;

or $R_5$ taken together with $R_2$ form an optionally substituted 5- to 12-membered nitrogen-containing heterocycle, which optionally incorporates from one to two additional heteroatoms, selected from N, O, and S in the heterocycle ring;

$R_7$ is chosen from optionally substituted alkyl, optionally substituted aryl, optionally substituted aralkyl, optionally substituted heteroaryl, and optionally substituted heteroaralkyl;

$R_{12}$ is chosen from hydrogen, optionally substituted alkyl, optionally substituted aryl, optionally substituted aralkyl, optionally substituted heteroaryl, and optionally substituted heteroaralkyl; and $R_4$ is chosen from hydrogen, optionally substituted alkyl, optionally substituted alkoxy, halogen, hydroxyl, nitro, cyano, optionally substituted amino, alkylsulfonyl, alkylsulfonamido, alkylthio, carboxyalkyl, aminocarbonyl, aryloxy, heteroaryloxy, optionally substituted N-heterocyclyl, optionally substituted aryl, optionally substituted aralkyl, optionally substituted heteroaralkyl and optionally substituted heteroaryl;

(Formula I including single stereoisomers and mixtures of stereoisomers);

a pharmaceutically acceptable salt of a compound of Formula I;

a pharmaceutically acceptable solvate of a compound of Formula I; or a pharmaceutically acceptable solvate of a pharmaceutically acceptable salt of a compound of Formula I.

In one aspect, the invention relates to methods for treating cellular proliferative diseases and other disorders that can be treated by inhibiting KSP by the administration of a therapeutically effective amount of a compound of Formula I; a pharmaceutically acceptable salt of a compound of Formula I; a pharmaceutically acceptable solvate of a compound of Formula I; or a pharmaceutically acceptable solvate of a pharmaceutically acceptable salt of a compound of Formula I. Such diseases and disorders include cancer, hyperplasia, restenosis, cardiac hypertrophy, immune disorders, fungal disorders and inflammation.

In another aspect, the invention relates to compounds useful in inhibiting KSP kinesin. The compounds have the structures shown above in Formula I; a pharmaceutically acceptable salt of a compound of Formula I; a pharmaceutically acceptable solvate of a compound of Formula I; or a pharmaceutically acceptable solvate of a pharmaceutically acceptable salt of a compound of Formula I. The invention also relates to pharmaceutical compositions comprising: a therapeutically effective amount of a compound of Formula I; a pharmaceutically acceptable salt of a compound of Formula I; a pharmaceutically acceptable solvate of a compound of Formula I; or a pharmaceutically acceptable solvate of a pharmaceutically acceptable salt of a compound of Formula I; and one or more pharmaceutical excipients. In another aspect, the composition further comprises a chemotherapeutic agent other than a compound of the present invention.

In an additional aspect, the present invention provides methods of screening for compounds that will bind to a KSP kinesin, for example compounds that will displace or compete with the binding of a compound of the invention. The methods comprise combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods comprise combining a compound of the invention, a KSP kinesin, and at least one candidate agent and determining the effect of the candidate agent on the KSP kinesin activity.

DETAILED DESCRIPTION OF THE INVENTION

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
CBZ=carbobenzoxy=benzyloxycarbonyl
DBU=diazabicyclo[5.4.0]undec-7-ene
DCM=dichloromethane=methylene chloride=$CH_2Cl_2$
DCE=dichloroethane
DEAD=diethyl azodicarboxylate
DIC=diisopropylcarbodiimide
DIEA=N,N-diisopropylethylamine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Et=ethyl
Fmoc=9-fluorenylmethoxycarbonyl
GC=gas chromatography
HATU=O-(7-Azabenzotriazol-1-yl)-1,1,3,3-tetramethyluronium hexafluorophosphate
HMDS=hexamethyldisilazane
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl
PhOH=phenol
PfP=pentafluorophenol PPTS=pyridinium p-toluenesulfonate
Py=pyridine
PyBroP=bromo-tris-pyrrolidino-phosphonium hexafluorophosphate
rt=room temperature
sat'd=saturated
s-=secondary
t-=tertiary
TBDMS=t-butyldimethylsilyl
TES=triethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl Alkyl is intended to include linear, branched, or cyclic aliphatic hydrocarbon structures and combinations thereof, which structures may be saturated or unsaturated. Lower-alkyl refers to alkyl groups of from 1 to 5 carbon atoms, preferably from 1 to 4 carbon atoms. Examples of lower-alkyl groups include methyl-, ethyl-, propyl-, isopropyl-, butyl-, s- and t-butyl and the like. Preferred alkyl groups are those of $C_{20}$ or below. More preferred alkyl groups are those of $C_{13}$ or below. Cycloalkyl is a subset of alkyl and includes cyclic aliphatic hydrocarbon groups of from 3 to 13 carbon atoms. Examples of cycloalkyl groups include c-propyl-, c-butyl-, c-pentyl-, norbornyl-, adamantyl and the like. Cycloalkyl-alkyl- is another subset of alkyl and refers to cycloalkyl attached to the parent structure through a non-cyclic alkyl-. Examples of cycloalkyl-alkyl- include cyclohexylmethyl-, cyclopropylmethyl-, cyclohexylpropyl-, and the like. In this application, alkyl includes alkanyl-, alkenyl and alkynyl residues; it is intended to include vinyl-, allyl-, isoprenyl and the like. When an alkyl residue having a specific number of carbons is named, all geometric isomers having that number of carbons are intended to be encompassed; thus, for example, "butyl" is meant to include n-butyl-, sec-butyl-, isobutyl and t-butyl-; "propyl" includes n-propyl-, isopropyl-, and c-propyl-.

Alkylene-, alkenylene-, and alkynylene- are other subsets of alkyl-, including the same residues as alkyl-, but having two points of attachment within a chemical structure. Examples of alkylene include ethylene (—CH$_2$CH$_2$—), propylene (—CH$_2$CH$_2$CH$_2$—), dimethylpropylene (—CH$_2$C(CH$_3$)$_2$CH$_2$—) and cyclohexylpropylene (—CH$_2$CH$_2$CH(C$_6$H$_{13}$)—). Likewise, examples of alkenylene include ethenylene (—CH═CH—), propenylene (—CH═CH—CH$_2$—), and cyclohexylpropenylene (—CH═CHCH(C$_6$H$_{13}$)—). Examples of alkynylene include ethynylene (—C≡C—) and propynylene (—CH═CH—CH$_2$—).

Cycloalkenyl is a subset of alkyl and includes unsaturated cyclic hydrocarbon groups of from 3 to 13 carbon atoms. Examples of cycloalkenyl groups include c-hexenyl-, c-pentenyl and the like.

Alkoxy or alkoxyl refers to an alkyl group, preferably including from 1 to 8 carbon atoms, of a straight, branched, or cyclic configuration, or a combination thereof, attached to the parent structure through an oxygen (i.e., the group alkyl-O—). Examples include methoxy-, ethoxy-, propoxy-, isopropoxy-, cyclopropyloxy-, cyclohexyloxy- and the like. Lower-alkoxy refers to alkoxy groups containing one to four carbons.

Acyl refers to groups of from 1 to 8 carbon atoms of a straight, branched, or cyclic configuration or a combination thereof, attached to the parent structure through a carbonyl functionality. Such groups may be saturated or unsaturated, and aliphatic or aromatic. One or more carbons in the acyl residue may be replaced by oxygen, nitrogen (e.g., carboxamido), or sulfur as long as the point of attachment to the parent remains at the carbonyl. Examples include acetyl-, benzoyl-, propionyl-, isobutyryl-, oxalyl-, t-butoxycarbonyl-, benzyloxycarbonyl, morpholinylcarbonyl, and the like. Lower-acyl refers to acyl groups containing one to four carbons.

Amino refers to the group —NH$_2$. The term "substituted amino" refers to the group —NHR or —NRR where each R is independently selected from the group: optionally substituted alkyl-, optionally substituted alkoxy, optionally substituted aminocarbonyl-, optionally substituted aryl-, optionally substituted heteroaryl-, optionally substituted heterocyclyl-, acyl-, alkoxycarbonyl-, sulfanyl-, sulfinyl and sulfonyl-, e.g., diethylamino, methylsulfonylamino, furanyl-oxy-sulfonamino. Substituted amino includes the groups NR$^c$COR$^b$, —NR$^c$CO$_2$R$^a$, and —NR$^c$CONR$^b$R$^c$, where R$^a$ is an optionally substituted $C_1$-$C_6$ alkyl-, aryl-, heteroaryl-, aryl-$C_1$-$C_4$ alkyl-, or heteroaryl-$C_1$-$C_4$ alkyl- group;

R$^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and R$^c$ is hydrogen or $C_1$-$C_4$ alkyl-; and where each optionally substituted R$^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halogen, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

Antimitotic refers to a drug for inhibiting or preventing mitosis, for example, by causing metaphase arrest. Some antitumour drugs block proliferation and are considered antimitotics.

Aryl and heteroaryl mean a 5- or 6-membered aromatic or heteroaromatic ring containing 0 or 1-4 heteroatoms, respectively, selected from O, N, or S; a bicyclic 9- or 10-membered aromatic or heteroaromatic ring system containing 0 or 1-4 (or more) heteroatoms, respectively, selected from O, N, or S; or a tricyclic 12- to 14-membered aromatic or heteroaromatic ring system containing 0 or 1-4 (or more) heteroatoms, respectively, selected from O, N, or S. The aromatic 6- to 14-membered carbocyclic rings include, e.g., phenyl-, naphthyl-, indanyl-, tetralinyl-, and fluorenyl and the 5- to 10-membered aromatic heterocyclic rings include, e.g., imidazolyl-, pyridinyl-, indolyl-, thienyl-, benzopyranonyl-, thiazolyl-, furanyl-, benzimidazolyl-, quinolinyl-, isoquinolinyl-, quinoxalinyl-, pyrimidinyl-, pyrazinyl-, tetrazolyl and pyrazolyl-.

Aralkyl- refers to a residue in which an aryl moiety is attached to the parent structure via an alkyl residue. Examples include benzyl-, phenethyl-, phenylvinyl-, phenylallyl and the like. Heteroaralkyl- refers to a residue in which a heteroaryl moiety is attached to the parent structure via an alkyl residue. Examples include furanylmethyl-, pyridinylmethyl-, pyrimidinylethyl and the like.

Aralkoxy- refers to the group —O-aralkyl. Similarly, heteroaralkoxy- refers to the group —O-heteroaralkyl-; aryloxy- refers to the group —O-aryl-; acyloxy- refers to the group —O-acyl-; heteroaryloxy- refers to the group —O-heteroaryl-; and heterocyclyloxy- refers to the group —O-heterocyclyl (i.e., aralkyl-, heteroaralkyl-, aryl-, acyl-, heterocyclyl-, or heteroaryl is attached to the parent structure through an oxygen).

Carboxyalkyl- refers to the group -alkyl-COOH.

Aminocarbonyl refers to the group —CONR$^b$R$^c$, where R$^b$ is H or optionally substituted $C_1$-$C_6$ alkyl-, aryl-, heteroaryl-, aryl-$C_1$-$C_4$ alkyl-, or heteroaryl-$C_1$-$C_4$ alkyl- group; and R$^c$ is hydrogen or $C_1$-$C_4$ alkyl-; and where each optionally substituted R$^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl, —$C_1$-$C_4$ alkyl-OH, —O$C_1$-$C_4$ haloalkyl, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl). Aminocarbonyl is meant to include carbamoyl-; lower-alkyl carbamoyl-; benzylcarbamoyl-; phenylcarbamoyl-; methoxymethyl-carbamoyl-; and the like.

Halogen or halo refers to fluorine, chlorine, bromine or iodine. Fluorine, chlorine and bromine are preferred. Dihaloaryl-, dihaloalkyl-, trihaloaryl etc. refer to aryl and alkyl substituted with the designated plurality of halogens (here, 2, 2 and 3, respectively), but not necessarily a plurality of the same halogen; thus 4-chloro-3-fluorophenyl is within the scope of dihaloaryl-.

Heterocyclyl means a cycloalkyl or aryl residue in which one to four of the carbons is replaced by a heteroatom such as oxygen, nitrogen or sulfur. Examples of heterocycles that fall within the scope of the invention include azetidinyl-, imidazolinyl-, pyrrolidinyl-, pyrazolyl-, pyrrolyl-, indolyl-, quinolinyl-, isoquinolinyl-, tetrahydroisoquinolinyl-, benzofuranyl-, benzodioxanyl-, benzodioxyl (commonly referred to as methylenedioxyphenyl-, when occurring as a substituent), tetrazolyl-, morpholinyl-, thiazolyl-, pyridinyl-, pyridazinyl-, piperidinyl-, pyrimidinyl-, thienyl-, furanyl-, oxazolyl-, oxazolinyl-, isoxazolyl-, dioxanyl-, tetrahydrofuranyl and the like. "N-heterocyclyl" refers to a nitrogen-containing heterocycle.

The term heterocyclyl encompasses heteroaryl-, which is a subset of heterocyclyl-. Examples of N-heterocyclyl residues include azetidinyl-, 4-morpholinyl-, 4-thiomorpholinyl-, 1-piperidinyl-, 1-pyrrolidinyl-, 3-thiazolidinyl-, piperazinyl and 4-(3,4-dihydrobenzoxazinyl). Examples of substituted heterocyclyl include 4-methyl-1-piperazinyl and 4-benzyl-1-piperidinyl-.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

Optional or optionally means that the subsequently described event or circumstance may or may not occur, and that the description includes instances where said event or circumstances occurs and instances in which it does not. For example, "optionally substituted alkyl" includes "alkyl" and "substituted alkyl" as defined herein. It will be understood by those skilled in the art with respect to any group containing one or more substituents that such groups are not intended to introduce any substitution or substitution patterns that are sterically impractical and/or synthetically non-feasible and/or inherently unstable.

Substituted alkoxy refers to alkoxy wherein the alkyl constituent is substituted (i.e., —O-(substituted alkyl)). One suitable substituted alkoxy group is "polyalkoxy" or —O-(optionally substituted alkylene)-(optionally substituted alkoxy), and includes groups such as —$OCH_2CH_2OCH_3$, and residues of glycol ethers such as polyethyleneglycol, and —O($CH_2CH_2O)_xCH_3$, where x is an integer of about 2-20, preferably about 2-10, and more preferably about 2-5. Another suitable substituted alkoxy group is hydroxyalkoxy or —$OCH_2(CH_2)_y$OH, where y is an integer of about 1-10, preferably about 1-4.

Substituted- alkyl-, aryl-, and heteroaryl- refer respectively to alkyl-, aryl-, and heteroaryl wherein one or more (up to about 5, preferably up to about 3) hydrogen atoms are replaced by a substituent independently selected from the group: —R$^a$, —OR$^b$, —O($C_1$-$C_2$ alkyl)O—(e.g., methylenedioxy- or ethylenedioxy-), —SR$^b$, guanidine, guanidine wherein one or more of the guanidine hydrogens are replaced with a lower-alkyl group, —NR$^b$R$^c$, halogen, cyano, nitro, —COR$^b$, —$CO_2$R$^b$, —CONR$^b$R$^c$, —OCOR$^b$, —$OCO_2$R$^a$, —OCONR$^b$R$^c$, —NR$^c$COR$^b$, —NR$^c$$CO_2$R$^a$, —NR$^c$CONR$^b$R$^c$, —$CO_2$R$^b$, —CONR$^b$R$^c$, —NR$^c$COR$^b$, —SOR$^a$, $SO_2$R$^a$, —$SO_2$NR$^b$R$^c$, and —NR$^c$$SO_2$R$^a$, where R$^a$ is an optionally substituted $C_1$-$C_6$ alkyl-, aryl-, heteroaryl-, aryl-$C_1$-$C_4$ alkyl-, or heteroaryl-$C_1$-$C_4$ alkyl- group, R$^b$ is H or optionally substituted $C_1$-$C_6$ allyl-, aryl-, heteroaryl-, aryl-$C_1$-$C_4$ alkyl-, or heteroaryl-$C_1$-$C_4$ alkyl- group;

R$^c$ is hydrogen or $C_1$-$C_4$ alkyl-;

where each optionally substituted R$^a$ group and R$^b$ group is independently unsubstituted or substituted with one or more substituents independently selected from $C_1$-$C_4$ alkyl-, aryl-, heteroaryl-, aryl-$C_1$-$C_4$ alkyl-, heteroaryl-$C_1$-$C_4$ alkyl-, $C_1$-$C_4$ haloalkyl-, —O$C_1$-$C_4$ alkyl-, —O$C_1$-$C_4$ alkylphenyl-, —$C_1$-$C_4$ alkyl-OH, —O$C_1$-$C_4$ haloalkyl-, halogen, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2$H, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl-, —C(O)$C_1$-$C_4$ phenyl-, —C(O)$C_1$-$C_4$ haloalkyl-, —OC(O)$C_1$-$C_4$ alkyl-, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl). In the compounds of Formula I where T and/or T' are substituted alkylene, the term "substituted" also refers to alkylene groups where one or more (up to about 3, particularly 1) carbon atoms are replaced by a heteroatom independently selected from O, N or S, such as —$CH_2$—S—$CH_2$—.

Sulfanyl refers to the groups: —S-(optionally substituted alkyl), —S-(optionally substituted aryl), —S-(optionally substituted heteroaryl), and —S-(optionally substituted heterocyclyl).

Sulfinyl refers to the groups: —S(O)—H, —S(O)-(optionally substituted alkyl), —S(O)-optionally substituted aryl), —S(O)-(optionally substituted heteroaryl), —S(O)-(optionally substituted heterocyclyl); and —S(O)-(optionally substituted amino).

Sulfonyl refers to the groups: —$S(O_2)$—H, —$S(O_2)$-(optionally substituted alkyl), —$S(O_2)$-optionally substituted aryl), —$S(O_2)$-(optionally substituted heteroaryl), —$S(O_2)$-(optionally substituted heterocyclyl), —$S(O_2)$-(optionally substituted alkoxy), —$S(O_2)$-optionally substituted aryloxy), —$S(O_2)$-(optionally substituted heteroaryloxy), —$S(O_2)$-(optionally substituted heterocyclyloxy); and —$S(O_2)$-(optionally substituted amino).

Pharmaceutically acceptable salts refers to those salts that retain the biological effectiveness of the free compound and that are not biologically undesirable or unsuitable for pharmaceutical use, formed with a suitable acid or base, and includes pharmaceutically acceptable acid addition salts and base addition salts. Pharmaceutically acceptable acid addition salts include those derived from inorganic acids such as hydrochloric acid, hydrobromic acid, sulfuric acid, nitric acid, phosphoric acid and the like, and those derived from organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Pharmaceutically acceptable base addition salts include those derived from inorganic bases such as sodium, potassium, lithium, ammonium, calcium, magnesium, iron, zinc, copper, manganese, aluminum salts and the like. Particular embodiments are the ammonium, potassium, sodium, calcium, and magnesium salts. Base addition salts also include those derived from pharmaceutically acceptable organic non-toxic bases, including salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

Protecting group has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxy protected form is where at least one of the hydroxyl groups present in a compound is protected with a hydroxy protecting group. Likewise, amines and other reactive groups may similarly be protected.

Solvate refers to the compound formed by the interaction of a solvent and a compound of Formula I or salt thereof. Suitable solvates of the compounds of the Formula I or a salt thereof are pharmaceutically acceptable solvates including hydrates.

Many of the compounds described herein contain one or more asymmetric centers (e.g. the carbon to which $R_2$ and $R_{2'}$ are attached where $R_2$ differs from $R_{2'}$) and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms and rotational isomers are also intended to be included.

When desired, the R- and S-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Compounds of the Present Invention

The present invention is directed to a class of novel compounds, that can be described as 1,2,4-triazin-5-one derivatives, that are inhibitors of one or more mitotic kinesins. By inhibiting mitotic kinesins, but not other kinesins (e.g., transport kinesins), specific inhibition of cellular proliferation is accomplished. While not intending to be bound by any theory, the present invention capitalizes on the finding that perturbation of mitotic kinesin function causes malformation or dysfunction of mitotic spindles, frequently resulting in cell cycle arrest and cell death. According to one embodiment of the invention, the compounds described herein inhibit the mitotic kinesin, KSP, particularly human KSP. In another embodiment, the compounds inhibit the mitotic kinesin, KSP, as well as modulating one or more of the human mitotic kinesins selected from the group consisting of HSET (see, U.S. Pat. No. 6,361,993, which is incorporated herein by reference); MCAK (see, U.S. Pat. No. 6,331,424, which is incorporated herein by reference); CENP-E (see, PCT Publication No. WO 99/13061, which is incorporated herein by reference); Kif4 (see, U.S. Pat. No. 6,440,684, which is incorporated herein by reference); MKLP1 (see, U.S. Pat. No. 6,448,025, which is incorporated herein by reference); Kif15 (see, U.S. Pat. No. 6,355,466, which is incorporated herein by reference); Kid (see, U.S. Pat. No. 6,387,644, which is incorporated herein by reference); Mpp1, CMKrp, KinI-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and RabK6.

The methods of inhibiting a mitotic kinesin comprise contacting an inhibitor of the invention with a kinesin, particularly a human kinesin, more particularly, human KSP or fragments and variants thereof. The inhibition can be of the ATP hydrolysis activity of the KSP kinesin and/or the mitotic spindle formation activity, such that the mitotic spindles are disrupted. Meiotic spindles may also be disrupted.

The present invention provides inhibitors of mitotic kinesins, in particular KSP and especially human KSP, for the treatment of disorders associated with cell proliferation. The compounds, compositions and methods described herein can differ in their selectivity and are used to treat diseases of cellular proliferation, including, but not limited to cancer, hyperplasias, restenosis, cardiac hypertrophy, immune disorders, fungal disorders and inflammation.

Accordingly, the present invention relates to methods employing one or more compounds represented by Formula I:

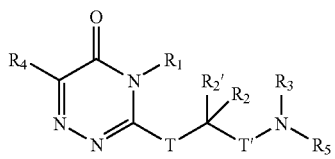

Formula I wherein:

T and T' are independently a covalent bond or optionally substituted lower alkylene;

$R_1$ is chosen from hydrogen, optionally substituted alkyl, optionally substituted aryl, optionally substituted aralkyl, optionally substituted heteroaryl, and optionally substituted heteroaralkyl;

$R_2$ and $R_{2'}$ are independently chosen from hydrogen, optionally substituted alkyl, optionally substituted aryl, optionally substituted aralkyl, optionally substituted heteroaryl, and optionally substituted heteroaralkyl; or $R_2$ and $R_{2'}$ taken together form an optionally substituted 3- to 7-membered ring;

$R_3$ is chosen from hydrogen, optionally substituted alkyl-, optionally substituted aryl-, optionally substituted aralkyl-, optionally substituted heteroaryl-, optionally substituted heteroaralkyl-, optionally substituted heterocyclyl, —C(O)—$R_6$, and —S(O)$_2$—$R_{6a}$;

$R_5$ is chosen from hydrogen, optionally substituted alkyl-, optionally substituted aryl-, optionally substituted aralkyl-, optionally substituted heteroaralkyl-, and optionally substituted heterocyclyl-;

$R_6$ is chosen from hydrogen, optionally substituted alkyl, optionally substituted aryl, optionally substituted aralkyl, optionally substituted heteroaryl, optionally substituted heteroaralkyl, $R_7O$— and $R_{12}$—NH—;

$R_{6a}$ is chosen from optionally substituted alkyl, optionally substituted aryl, optionally substituted aralkyl, optionally substituted heteroaryl, optionally substituted heteroaralkyl, and $R_{12}$—NH—;

or $R_5$ taken together with $R_3$, and the nitrogen to which they are bound, form an optionally substituted 5- to 12-membered nitrogen-containing heterocycle, which optionally incorporates from one to two additional heteroatoms, selected from N, O, and S in the heterocycle ring;

or $R_5$ taken together with $R_2$ form an optionally substituted 5- to 12-membered nitrogen-containing heterocycle, which optionally incorporates from one to two additional heteroatoms, selected from N, O, and S in the heterocycle ring;

$R_7$ is chosen from optionally substituted alkyl, optionally substituted aryl, optionally substituted aralkyl, optionally substituted heteroaryl, and optionally substituted heteroaralkyl;

$R_{12}$ is chosen from hydrogen, optionally substituted alkyl, optionally substituted aryl, optionally substituted aralkyl, optionally substituted heteroaryl, and optionally substituted heteroaralkyl; and $R_4$ is chosen from hydrogen, optionally substituted alkyl, optionally substituted alkoxy, halogen, hydroxyl, nitro, cyano, optionally substituted amino, alkylsulfonyl, alkylsulfonamido, alkylthio, carboxyalkyl, aminocarbonyl, aryloxy, heteroaryloxy, optionally substituted N-heterocyclyl, optionally substituted aryl, optionally substituted aralkyl, optionally substituted heteroaralkyl and optionally substituted heteroaryl;

(Formula I including single stereoisomers and mixtures of stereoisomers);

a pharmaceutically acceptable salt of a compound of Formula I;

a pharmaceutically acceptable solvate of a compound of Formula I; or a pharmaceutically acceptable solvate of a pharmaceutically acceptable salt of a compound of Formula I. In a particular embodiment, the stereogenic center to which $R_2$ and $R_{2'}$ are attached is of the R configuration.

Nomenclature

The compounds of Formula I are named and numbered as described below. For example, the compound:

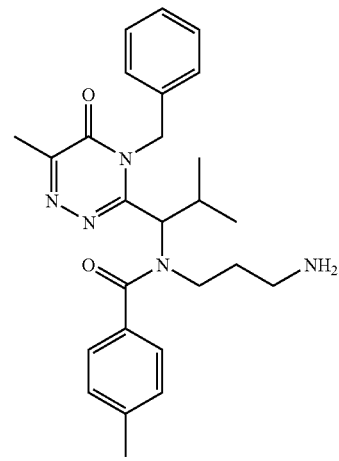

i.e., the compound according to Formula I where T and T' are absent, $R_1$ is benzyl, $R_2$ is propyl (specifically, i-propyl), $R_{2'}$ is hydrogen; $R_3$ is —C(O)$R_6$; $R_4$ is methyl; $R_5$ is aminopropyl; and $R_6$ is p-tolyl can be named N-(3-aminopropyl)-N-[1-(4-benzyl-6-methyl-5-oxo-4,5-dihydro-[1,2,4]triazin-3-yl)-2-methyl-propyl]-4-methyl-benzamide.

Likewise, the compound

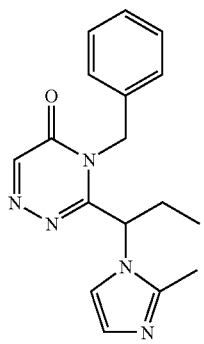

i.e., the compound according to Formula I where T and T' are absent, $R_1$ is benzyl, $R_2$ is ethyl, $R_{2'}$ is hydrogen; $R_3$ and $R_5$ taken together form a substituted imidazolyl; and $R_4$ is hydrogen can be named 4-benzyl-3-[1-(2-methyl-imidazol-1-yl)-propyl]-4H-[1,2,4]triazin-5-one.

Synthetic Reaction Parameters

The compounds of Formula I can be prepared by following the procedures described with reference to the Reaction Schemes below.

Unless specified otherwise, the terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%). In general, esters of carboxylic acids may be prepared by conventional esterification procedures, for example alkyl esters may be prepared by treating the required activated carboxylic acid with the appropriate alkanol, generally under acidic conditions. Likewise, amides may be prepared using conventional amidation procedures, for example amides may be prepared by treating an activated carboxylic acid with the appropriate amine. Alternatively, a lower-alkyl ester such as a methyl ester of the acid may be treated with an amine to provide the required amide, optionally in presence of trimethylalluminium following the procedure described in Tetrahedron Lett. 48, 4171-4173, (1977). Carboxyl groups may be protected as alkyl esters, for example methyl esters, which esters may be prepared and removed using conventional procedures, one convenient method for converting carbomethoxy to carboxyl is to use aqueous lithium hydroxide.

The salts and solvates of the compounds mentioned herein may as required be produced by methods conventional in the art. For example, if an inventive compound is an acid, a desired base addition salt can be prepared by treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine; as well as inorganic salts derived from sodium, calcium, potassium, magnesium, manganese, iron, copper, zinc, aluminum, and lithium.

If a compound is a base, a desired acid addition salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formula I

The compounds of Formula I can be prepared by following the procedures described with reference to the Reaction Schemes below. See, also, PCT WO 03/39460, WO 03/49678, WO 03/50122, WO 03/49527, WO 0349679, WO 03/50064, each of which is incorporated herein by reference for all purposes.

Brief Description of Reaction Schemes

Reaction Scheme 1 illustrates synthesis of compounds of Formula I wherein $R_3$ is —C(O)$R_6$.

Reaction Scheme 2 illustrates a synthesis of compounds of Formula I wherein $R_3$ is —SO$_2$$R_{6a}$.

Reaction Scheme 3 illustrates a synthesis of compounds of Formula I.

Reaction Scheme 4 illustrates a synthesis of compounds of Formula I wherein $R_3$ and $R_5$ taken together form an optionally substituted imidazolyl.

Reaction Scheme 5 illustrates an alternative synthesis of compounds of Formula I wherein $R_3$ and $R_5$ taken together form optionally substituted imidazolyl.

Reaction Scheme 6 illustrates a synthesis of compounds of Formula I wherein $R_3$ and $R_5$ taken together form optionally substituted imidazolinyl.

Reaction Scheme 7 illustrates an alternative synthesis of compounds of Formula I wherein $R_3$ and $R_5$ taken together form is optionally substituted imidazolinyl.

Reaction Scheme 8 illustrates a synthesis of compounds of Formula I wherein $R_3$ and $R_5$ taken together form is optionally substituted diazepanone ring.

Reaction Scheme 9 illustrates another synthesis of compound of Formula I wherein $R_3$ and $R_5$ taken together form is optionally substituted diazepanone ring.

Reaction Scheme 10 illustrates a synthesis of compounds of Formula I wherein $R_3$ and $R_5$ taken together form is optionally substituted piperazine ring Starting Materials The protected α-amino acids of Formula 101 and other reactants are commercially available, e.g., from Aldrich Chemical Company, Milwaukee, Wis., or may be readily prepared by those skilled in the art using commonly employed synthetic methodology.

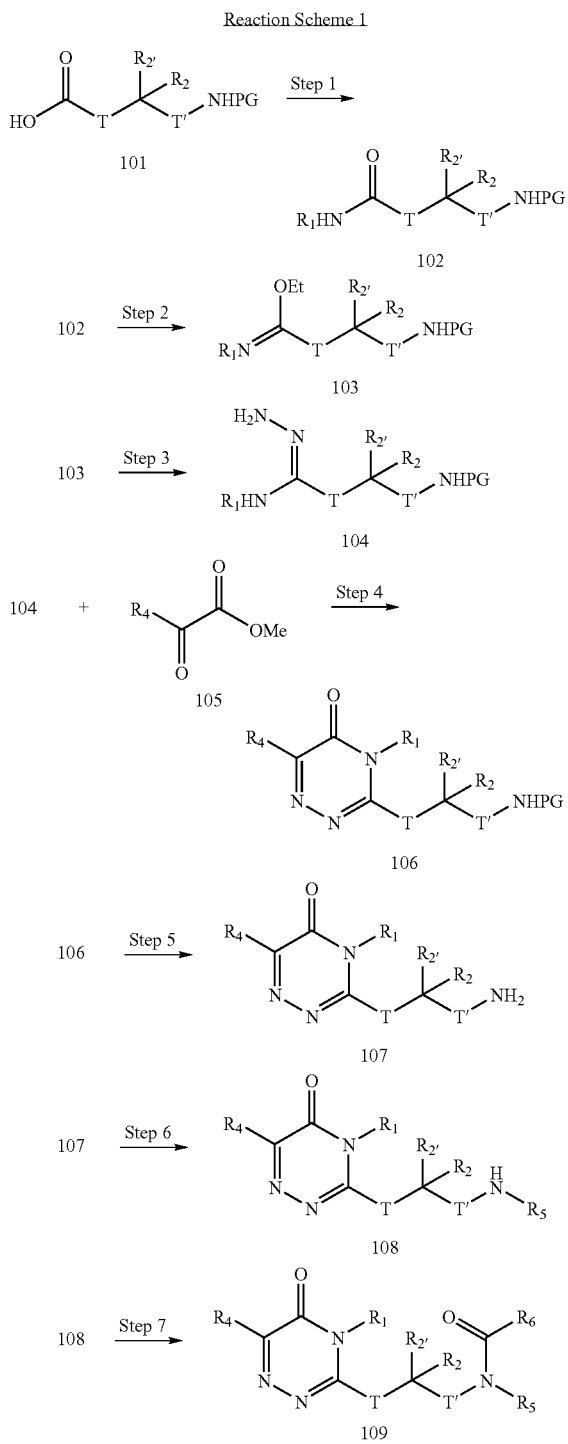

Reaction Scheme 1

Preparation of Formula 102

Referring to Reaction Scheme 1, Step 1, to a solution of a suitably protected α-amino acid (the compound of Formula 101, preferably wherein protecting group, PG, is CBZ) in an inert organic solvent (such as THF) is added ethyl chloroformate and a tertiary amine base (such as triethylamine or DIEA) at 0° C. The reaction mixture is stirred under nitrogen. After 1 hour, a primary amine with the formula of $R_1$—$NH_2$ (where $R_1$ is described as above) is added over 5-10 minutes. Upon completion of addition, the reaction solution is allowed to warm to room temperature. The reaction mixture is stirred for 1-4 hours. The optionally substituted α-amino amide (the compound of Formula 102) is isolated and purified.

Preparation of Formula 103

Referring to Reaction Scheme 1, Step 2, a solution of a compound of Formula 102 and Meerwein's salt (such as triethyloxonium hexafluorophosphate) in dichloromethane is stirred for 14-24 hours. The product, an imidate of Formula 103, is isolated and used in the next step without further purifaction.

Preparation of Formula 104

Referring to Reaction Scheme 1, Step 3, to a solution of an imidate of Formula 103 in a polar, aprotic solvent (such as THF) is added a solution of hydrazine in THF. The reaction mixture is stirred for about 4-9 hours. The product, a hydrazidine of Formula 104, is isolated and purified.

Preparation of Formula 106

Referring to Reaction Scheme 1, Step 4, a solution of a hydrazidine of Formula 104 and a reagent of Formula 105 in EtOH or toluene is refluxed for 4-10 hours. A catalytic amount of acetic acid is added. Refluxing continues for additional 6-10 hours. The product, a 1,2,4-triazin-5-one of Formula 106, is isolated and purified.

Preparation of Formula 107

Referring to Reaction Scheme 1, Step 5, the amino-protecting group of a compound of Formula 106 is removed. For example, to a solution of a 1,2,4-triazin-5-one of Formula 106 wherein the amino protecting group, PG, is CBZ in a polar solvent such as methanol is added 10% Pd on carbon. The reaction mixture is stirred under a stream of $H_2$ (20-40 psi) for 40 minutes to 2 hours. The product, a compound of Formula 107, is isolated and used in the next step without further purification. One of skill in the art will readily appreciate that the removal of other protecting groups can be accomplished using conditions known in the art. See, e.g., Greene, et al. supra.

Preparation of Formula 108

Referring to Reaction Scheme 1, Step 6, to a solution of a 1,2,4-triazin-5-one of Formula 107 is added successively a slight excess (preferably about 1.2 equivalents) of an aldehyde comprising $R_{5'}$ (i.e., a compound having the formula $R_5CHO$ where $R_5CH_2$— is equivalent to $R_5$ and $R_5$ is as described above or is a protected precursor to such a substituent, e.g., (3-oxo-propyl)-carbamic acid tert-butyl ester) and a reducing agent such as sodium triacetoxyborohydride. The resulting mixture is stirred for several hours. The product, a 1,2,4-triazin-5-one of Formula 108, is isolated and purified.

Preparation of Formula 109

Referring to Reaction Scheme 1, Step 7, to a solution of a 1,2,4-triazin-5-one of Formula 108 and an amine base such as diisopropylethylamine in a polar, aprotic solvent such as dichloromethane is added an $R_6$ acyl chloride (such as Cl—C(O)—$R_6$ where $R_6$ is as described above). The resulting solution is stirred under nitrogen at room temperature for several hours. The product, a 1,2,4-triazin-5-one of Formula 109, is isolated and purified.

Optionally, any protecting groups on a compound of Formula 109 are then removed. For example, if $R_5$ comprises a protected amine wherein the protecting group is a Boc group, then to a solution of a 1,2,4-triazin-5-one of Formula 109 in a polar, aprotic solvent such as dichloromethane is added trifluoroacetic acid, while maintaining the reaction at about room temperature. The reaction is monitored, e.g., by TLC. Upon completion, the product, the free amine, is isolated and purified.

Preparation of Optically Active Compounds

In certain compounds of the invention, a particular stereo configuration (such as the (R) isomer) may be preferred at the stereogenic center to which $R_2$ is attached. The optically active compound can be prepared by methods known in the art. For example, an amine of Formula 107 is dissolved in an inert organic solvent (such as IPA) and warmed to 60° C. In a separate vessel, a resolving agent (such as dibenzoyl-D-tartaric acid) is dissolved, preferably in the same warm solvent, and then quickly added (with agitation) to the warm amine solution. The reaction mixture is left to crystallize by cooling to room temperature over 16 hours under continuing agitation. The desired isomer, e.g., the (R) isomer is isolated and purified.

For the sake of brevity in the remaining description of the synthesis of compounds of Formula I, it should be understood that either single isomer or a mixture of isomers may be employed to give the corresponding product.

Reaction Scheme 2

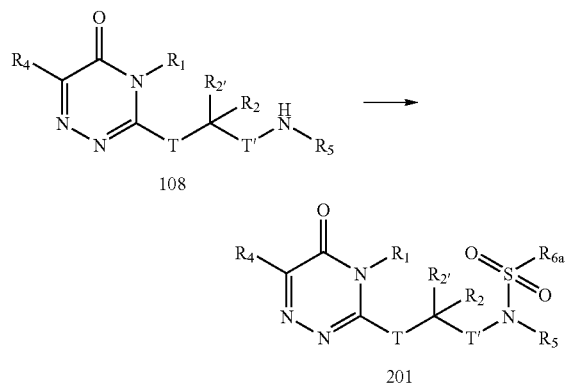

Referring to Reaction Scheme 2, to a solution of a 1,2,4-triazin-5-one of Formula 108 and an amine base (such as diisopropylethylamine) in a polar, aprotic solvent (such as dichloromethane) is added a compound having the formula Cl—S(O)$_2$R$_{6a}$ or O—(S(O)$_2$—R$_{6a}$)$_2$ where R$_{6a}$ is as described above. The resulting solution is stirred under nitrogen at room temperature for several hours. The product, a 1,2,4-triazin-5-one of Formula 201 is isolated and purified.

Reaction Scheme 3

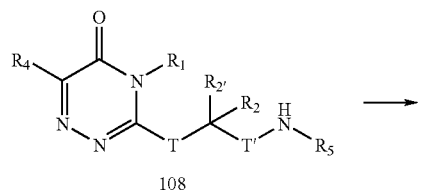

-continued

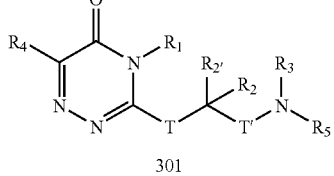

Referring to Reaction Scheme 3, to a solution of a 1,2,4-triazin-5-one of Formula 108 and an amine base (such as diisopropylethylamine) in a polar, aprotic solvent (such as dichloromethane) is added a compound having the formula X—R$_3$ wherein X is a leaving group and R$_3$ is as described above. The resulting solution is stirred under nitrogen at room temperature or with heat for several hours. The product, a 1,2,4-triazin-5-one of Formula 301 is isolated and purified.

Reaction Scheme 4

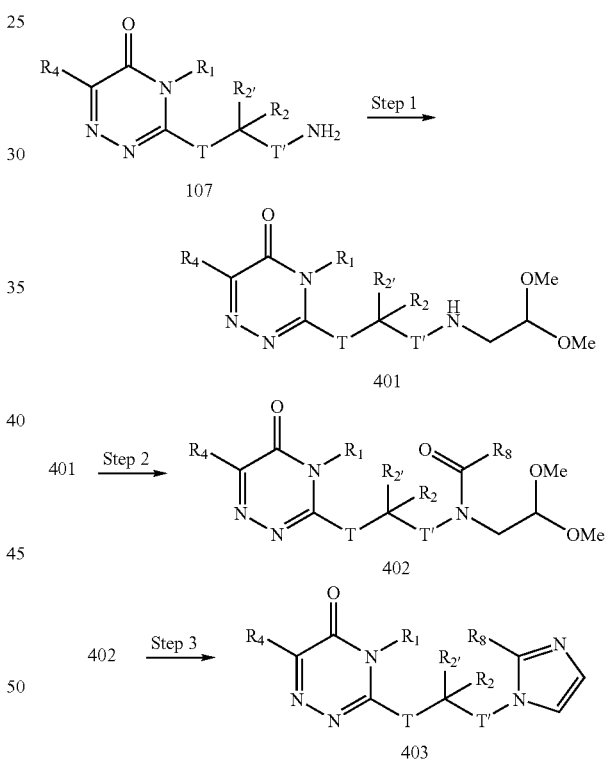

Preparation of Formula 401

Referring to Reaction Scheme 4, Step 1, to an optionally substituted compound of Formula 107 dissolved in a polar, aprotic solvent (such as DMF) in the presence of a base (such as potassium carbonate) is added one equivalent of an optionally substituted suitably protected aldehyde wherein such aldehyde further comprises a leaving group, preferably, a halide. The solution is heated at reflux, monitoring completion of the reaction (e.g., by TLC). The reaction mixture is cooled and the corresponding, optionally substituted 1,2,4-triazin-5-one of Formula 401 is isolated and purified.

Preparation of Formula 402

Referring to Reaction Scheme 4, Step 2, to an optionally substituted compound of Formula 401 in an inert solvent (such as dichloromethane) in the presence of about 1.5 molar equivalents of an amine base (such as triethylamine) is added about 1.5 molar equivalents of an $R_8$ acid chloride, such as, Cl—C(O)—$R_8$, where $R_8$ is as described below. The reaction takes place, with stirring, at room temperature over a period of 4 to 24 hours. Completion is monitored, e.g., by TLC. The corresponding compound of Formula 402 is isolated and purified.

Preparation of Formula 403

Referring to Reaction Scheme 4, Step 3, a solution of a compound of Formula 402 and an excess of ammonium acetate in acetic acid is heated at reflux for 1-4 hours. Completion is monitored, e.g., by TLC. The corresponding compound of Formula 403 is isolated and purified.

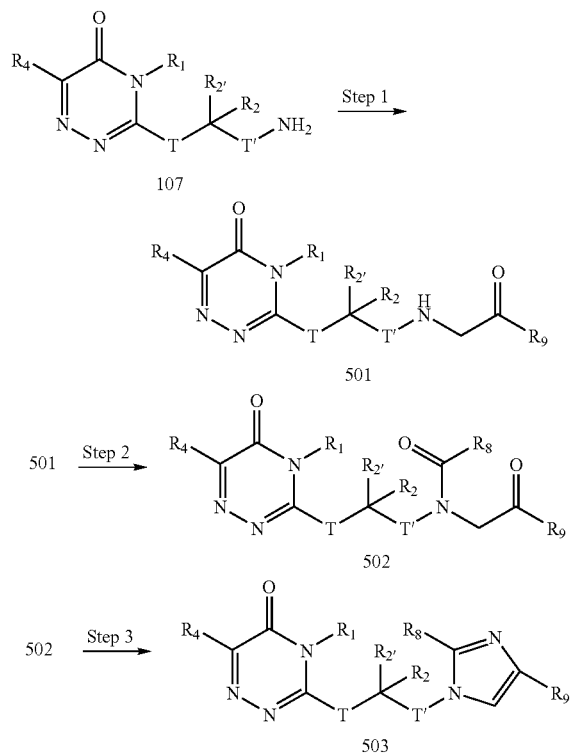

Preparation of Formula 501

Referring to Reaction Scheme 5, Step 1, a suspension of a compound of Formula 107, an alpha-haloketone reagent of the Formula $R_9(CO)CH_2X$ wherein X is a halide, and about an equivalent of a base, such as potassium carbonate in a polar, aprotic solvent such as DMF is stirred at room temperature. The reaction is diluted with water and the resulting solid, a compound of Formula 501, is used in the subsequent step without further purification.

Preparation of Formula 502

Referring to Reaction Scheme 5, Step 2, a solution of the compound of Formula 501, about an equivalent of an amine base, such as triethylamine and about an equivalent of an acid chloride (such as a compound of Formula $R_8$—COCl) in an organic solvent such as methylene chloride is stirred at room temperature for several hours. Completion is monitored, e.g., by TLC. The corresponding compound of Formula 502 is isolated and purified.

Preparation of Formula 503

Referring to Reaction Scheme 5, Step 3, a solution of a compound of Formula 502 and an excess of ammonium acetate in acetic acid is heated at reflux using a Dean-Stark trap and condenser. Completion is monitored, e.g., by TLC. The corresponding compound of Formula 503 is isolated and purified.

Optionally, any protecting groups on compounds of Formula 503 are then removed. For example, if a phthalidmide protecting group is used, it may be removed as follows. A solution of a compound of Formula 503 and an excess of anhydrous hydrazine in a polar, protic solvent such as ethanol is heated at reflux. The reaction is cooled to about 5° C. and any precipitate is filtered off. The filtrate is concentrated in vacuo and purified to yield the corresponding free amine. One of skill in the art will appreciate that other conditions may be used to remove other protecting groups.

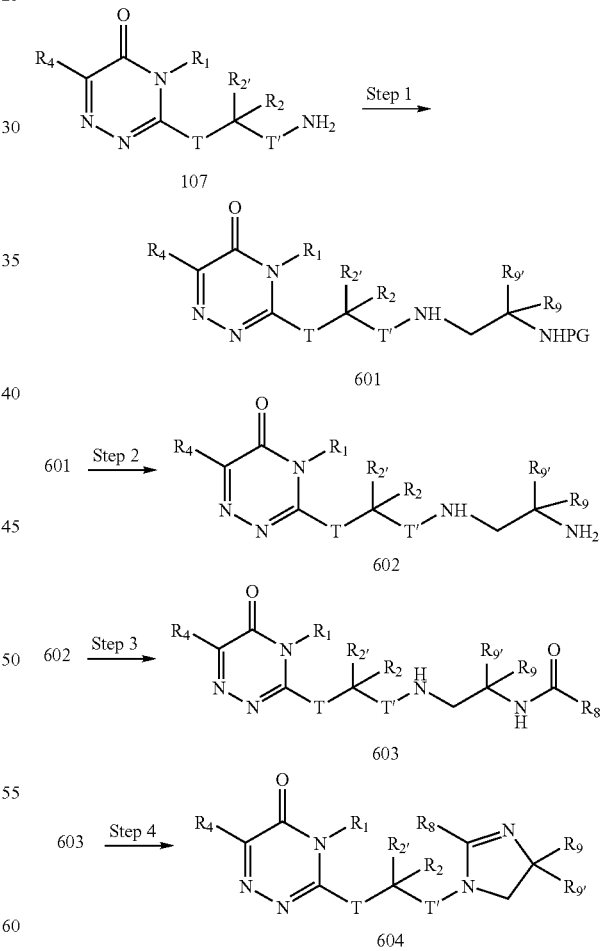

Preparation of Formula 601

Referring to Reaction Scheme 6, Step 1, reductive amination of amines of Formula 107 with an optionally substituted, aldehyde-containing carbamic acid ester (Seki et. al.

*Chem. Pharm. Bull.* 1996, 44, 2061) gives urethane intermediates. Removal of the Boc protecting group furnishes an amine of Formula 601.

More specifically, to a solution of a compound of Formula 107 and an equivalent of a suitably protected aldehyde (Seki et. al. *Chem. Pharm. Bull.* 1996, 44, 2061) in dichloromethane is added a slight excess of a reducing agent, such as sodium triacetoxyborohydride. The resultant cloudy mixture is maintained at ambient temperature. Completion is monitored, e.g., by TLC. The corresponding compound of Formula 601 is isolated and used in the subsequent step without purification.

Preparation of Formula 602

Referring to Reaction Scheme 6, Step 2, to a solution of a compound of Formula 601 in a polar, aprotic solvent such as dichloromethane is added a strong acid such as trifluoroacetic acid. The resultant solution is maintained at ambient temperature overnight and concentrated under reduced pressure. The residue is isolated to give a compound of Formula 602 which is used in the subsequent step without purification.

Preparation of Formula 603

Referring to Reaction Scheme 6, Step 3, to a solution of a compound of Formula 602 in a polar, aprotic solvent such as dichloromethane is added an excess, preferably about two equivalents of an amine base such as triethylamine, followed by about an equivalent or slight excess of an acid chloride of the Formula $R_8C(O)Cl$. The resultant solution is stirred at ambient temperature for about 3 hours. Completion is monitored, e.g., by TLC. The corresponding compound of Formula 603 is isolated and purified.

Preparation of Formula 604

Referring to Reaction Scheme 6, Step 4, a solution of a compound of Formula 603 in an excess of phosphorus oxychloride is heated at reflux. After 8 hours, the reaction mixture is allowed to cool to ambient temperature and concentrated under reduced pressure. The corresponding compound of Formula 604 is isolated and purified.

Reaction Scheme 7

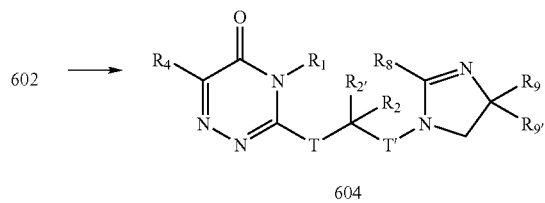

604

Preparation of Formula 604

As an alternative to Steps 3 and 4 of Reaction Scheme 6, acylation of primary amines of Formula 602, followed by acetic acid mediated cyclization, can proceed without isolation of the intermediate amides to provide the target compound of Formula 604. This route is shown in Reaction Scheme 7.

More specifically, to a solution of a compound of Formula 602 in a polar, aprotic solvent such as dichloromethane is added an excess, preferably about two equivalents of an amine base, such as triethylamine, followed by about an equivalent of an acid chloride. The resultant solution is stirred at ambient temperature for 2 hours, then evaporated under reduced pressure. The resultant solid is treated with glacial acetic acid, then the resultant suspension is heated at reflux for about 48 hours. The reaction is cooled to ambient temperature then evaporated under reduced pressure. The corresponding compound of Formula 604 is isolated and purified.

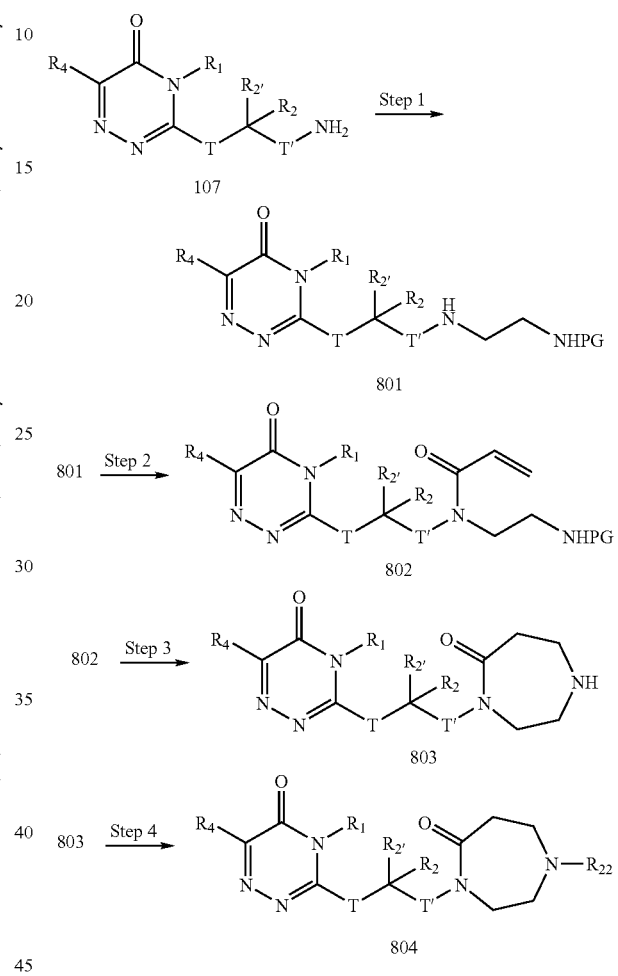

Referring to Reaction Scheme 8, reductive amination of the primary amino group in compounds of Formula 107 with (2-oxo-ethyl)-carbamic acid tert-butyl ester gives the corresponding secondary amine. Acylation with acryloyl chloride followed by deprotection of the tertiary amine and base mediated cyclisation gives the desired diazepanones. If desired, further functionalization of the basic amine can be accomplished under conditions well known to those skilled in the art.

Reaction Scheme 9

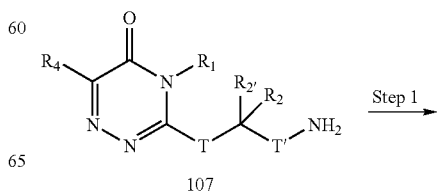

107

-continued

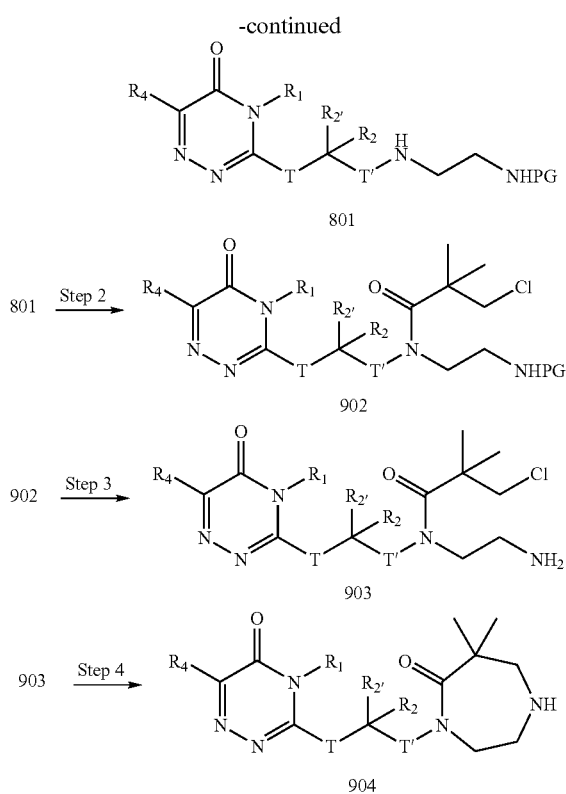

Referring to Reaction Scheme 9, reductive amination of the primary amino group in compounds of Formula 107 with (2-oxo-ethyl)-carbamic acid tert-butyl ester gives the corresponding secondary amine. Acylation with chloropivaloyl chloride followed by deprotection of the tertiary amide and base mediated cyclisation gives the desired diazepanones. If desired, further functionalization of the basic amine can be accomplished under conditions well known to those skilled in the art.

Reaction Scheme 10

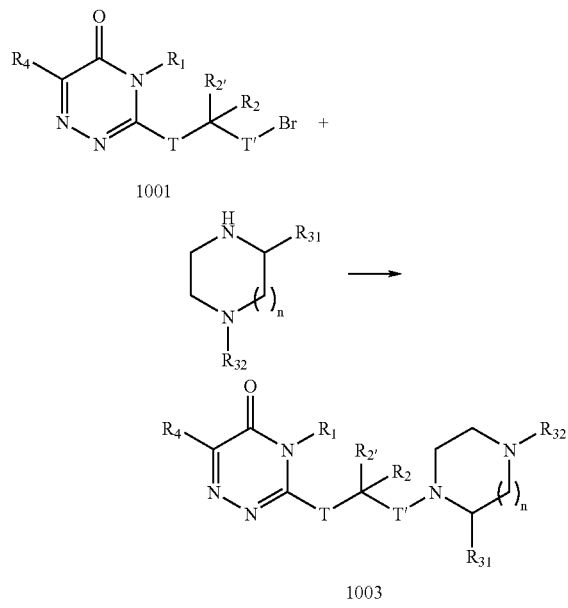

Referring to Reaction Scheme 10, a compound of Formula 1001, one-half molar equivalent of an optionally substituted piperazine or diazepam (as shown above, where $R_{32}$ is as described herein) and an excess of potassium carbonate are combined in an organic solvent (e.g., acetonitrile). The reaction takes place under a nitrogen atmosphere at elevated temperature (e.g., 100° C.) over a period of 8 hours, followed at a somewhat lower temperature (e.g., 60° C.) for a period of 5 days. The product, a compound of Formula 1003, is isolated and purified.

Optionally, in the event that $R_{32}$ is an amine protecting group, such as Boc, it may be removed by for example treatment with a 95/5 mixture of TFA/water followed by stirring at room temperature for 1 hour. The product, a compound of Formula 1003 wherein $R_{32}$ is hydrogen, can be isolated and purified. If desired, further functionalization of the basic amine could be accomplished under conditions well known to those skilled in the art.

Particular Processes and Last Steps

A compound of Formula I is optionally contacted with a pharmaceutically acceptable acid or base to form the corresponding acid or base addition salt.

A pharmaceutically acceptable acid addition salt of a compound of Formula I is optionally contacted with a base to form the corresponding free base of Formula I.

A pharmaceutically acceptable base addition salt of a compound of Formula I is optionally contacted with an acid to form the corresponding free acid of Formula I.

Particular Compounds

T and T'

When considering the compounds of Formula I, T is optionally substituted alkylene or is a covalent bond (i.e., is absent); and T' is optionally substituted alkylene or is absent. In one embodiment, one of T and T' is absent (i.e., is a covalent bond) and the other is optionally substituted alkylene (especially optionally substituted methylene). In another embodiment, both are absent.

$R_1$

When considering the compounds of Formula I, in a particular embodiment, $R_1$ is selected from hydrogen, optionally substituted $C_1$-$C_8$ alkyl, optionally substituted aryl, optionally substituted heteroaryl, optionally substituted aryl-$C_1$-$C_4$-alkyl-, and optionally substituted heteroaryl-$C_1$-$C_4$-alkyl- (especially, optionally substituted aryl and optionally substituted aryl-$C_1$-$C_4$-alkyl-). In a more particular embodiment $R_1$ is selected from hydrogen, optionally substituted $C_1$-$C_4$ alkyl, optionally substituted phenyl-$C_1$-$C_4$-alkyl-, optionally substituted naphthylmethyl, optionally substituted phenyl, and naphthyl. More particularly, $R_1$ is optionally substituted phenyl-$C_1$-$C_4$-alkyl- or optionally substituted heteroaryl-$C_1$-$C_4$-alkyl-.

In a most particular embodiment $R_1$ is naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, chlorobenzyl, methylbenzyl, methoxybenzyl, cyanobenzyl, hydroxybenzyl, dichlorobenzyl, dimethoxybenzyl, or naphthylmethyl. More particularly, $R_1$ is benzyl, halobenzyl, methylbenzyl, methoxylbenzyl, cyanobenzyl, hydroxybenzyl, or naphthylmethyl. Most particularly, $R_1$ is benzyl $R_2$ When considering the compounds of Formula I and as will be appreciated by those skilled in the art, the compounds described herein possess a potentially chiral center at the carbon to which $R_2$ and $R_{2'}$ are attached. The $R_2$ and $R_{2'}$ groups may be the same or different; if different, the compound is chiral (i.e., has a stereogenic center). When $R_2$ and $R_{2'}$ are different, in particular embodiments $R_{2'}$ is hydrogen and $R_2$ is other than hydrogen. The invention contemplates the use of pure enantiomers and mixtures of enantiomers, including racemic mixtures, although the use of a substantially optically pure enantiomer will generally be preferred. The term "substantially optically pure" or "enantiomerically pure" means having at least about 95% of the described enantiomer with no single impurity greater than about 1% and particularly, at least about 97.5% enantiomeric excess. In a particular embodiment, the stereogenic center to which $R_2$ and $R_{2'}$ are attached is of the R configuration.

In one embodiment, $R_2$ is optionally substituted $C_1$-$C_4$ alkyl, and $R_{2'}$ is hydrogen or optionally substituted $C_1$-$C_4$ alkyl. More particularly, $R_{2'}$ is hydrogen and $R_2$ is optionally substituted $C_1$-$C_4$ alkyl. In a most particular embodiment $R_2$ is chosen from methyl, ethyl, propyl (particularly, c-propyl or i-propyl), butyl (particularly, t-butyl), methylthioethyl, methylthiomethyl, aminobutyl, (CBZ)aminobutyl, cyclohexylmethyl, benzyloxymethyl, methylsulfinylethyl, methylsulfinylmethyl, and hydroxymethyl, and $R_{2'}$ is hydrogen. Especially preferred is when $R_{2'}$ is hydrogen and $R_2$ is ethyl or propyl (particularly, c-propyl or i-propyl). More particularly, $R_2$ is i-propyl. More preferred is the embodiment wherein the stereogenic center to which $R_2$ and $R_{2'}$ is attached is of the R configuration.

In another embodiment, both $R_2$ and $R_{2'}$ are hydrogen.

$R_2$ Taken Together with $R_5$

In another embodiment, $R_2$ and $R_5$ taken together form a 5- to 12-membered ring which optionally incorporates from one to two additional heteroatoms, selected from N, O, and S in the heterocycle ring and may optionally be substituted one or more of the following groups: alkyl, aryl, aralkyl, heteroaryl, substituted alkyl, substituted aryl, substituted aralkyl, and substituted heteroaryl.

In a particular embodiment, $R_2$ and $R_5$ taken together form an optionally substituted ring of the formula:

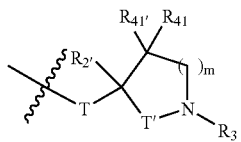

wherein $R_{41}$ and $R_{41'}$ are independently chosen from hydrogen, alkyl, aryl, aralkyl, heteroaryl, substituted alkyl, substituted aryl, substituted aralkyl, and substituted heteroaryl; m is 0, 1, 2, or 3; and T, T', $R_3$, and $R_{2'}$ are as defined above. In a more particular embodiment, $R_{41}$ is hydrogen. In another particular embodiment, both $R_{41}$ and $R_{41'}$ are hydrogen. In another embodiment, $R_3$ is optionally substituted aralkyl (especially benzyl) or optionally substituted acyl (especially p-methyl-benzoyl). See, e.g., U.S. Ser. No. 60/414,756, which is incorporated herein by reference for all purposes.

In another embodiment, $R_2$ and $R_5$ taken together form an optionally substituted ring of the formula:

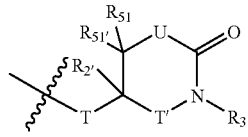

wherein $R_3$, $R_{2'}$, T, and T' are as defined above; $R_{51}$ and $R_{51'}$ are independently chosen from hydrogen, alkyl, aryl, aralkyl, heteroaryl, substituted alkyl, substituted aryl, substituted aralkyl and substituted heteroaryl; U is a covalent bond, CR'R" or NR'''; R' and R" are independently chosen from hydrogen, hydroxy, amino, optionally substituted aryl, optionally substituted alkylamino, optionally substituted alkyl and optionally substituted alkoxy; and R''' is chosen from hydrogen, optionally substituted alkyl, optionally substituted aryl, optionally substituted aralkyl, optionally substituted heteroaryl, and optionally substituted heteroaralkyl, provided that U is not a covalent bond when T' is absent.

In a particular embodiment, $R_{51}$ is hydrogen or optionally substituted lower alkyl; more particularly, $R_{51}$ is hydrogen. In another embodiment, $R_{51'}$ is hydrogen or optionally substituted lower alkyl; more particularly, $R_{51'}$ is hydrogen.

In one embodiment, $R_3$ is optionally substituted aryl or optionally substituted aralkyl; more particularly, $R_3$ is optionally substituted phenyl, benzyl or methyl-benzyl (especially, benzyl or methyl-benzyl). In another embodiment, $R_3$ is —C(O)$R_6$ and $R_6$ is optionally substituted aryl or optionally substituted aralkyl.

In one embodiment, U is CR'R" where R' and/or R" are hydrogen. In another embodiment, U is NR''' where R''' is hydrogen or optionally substituted alkyl. More particularly, R''' is hydrogen or optionally substituted amino-lower alkyl. See, e.g., U.S. Ser. No. 60/398,224, which is incorporated herein by reference for all purposes.

$R_4$

In a particular embodiment, $R_4$ is hydrogen, halo, hydroxyl, optionally substituted lower allyl (particularly, methyl or trifluoromethyl), optionally substituted aryl (particularly, phenyl), alkoxy (particularly, methoxy), cyano, substituted amino, carbamyl, aryloxy (particularly, phenoxy), heteroaryloxy (particularly, pyridinyloxy), heteroaryl (particularly, 2-oxo-2H-pyridinyl), or optionally substituted N-heterocyclyl (particularly, morpholinyl or piperazinyl). More particularly, $R_4$ is chosen from hydrogen, hydroxyl, halo (particularly chloro and fluoro), optionally substituted lower alkyl (particularly methyl), lower alkoxy (particularly methoxy), optionally substituted phenyl, and cyano. Most particularly, $R_4$ is optionally substituted methyl or optionally substituted phenyl.

$R_3$

In another embodiment, $R_3$ is chosen from optionally substituted $C_1$-$C_{13}$ alkyl (especially substituted $C_1$-$C_4$ alkyl); optionally substituted aralkyl (especially optionally substituted benzyl or maphthylmethyl-); and optionally substituted heteroaralkyl. More particularly, $R_3$ is benzyl or benzyl substituted with one or more of the following groups: carboxy, alkoxycarbonyl cyano, halo, $C_1$-$C_4$ alkyl-, $C_1$-$C_4$ alkoxy, nitro, methylenedioxy, or trifluoromethyl.

In another embodiment, $R_3$ is —C(O)—$R_6$ or S(O)$_2$—$R_{6a}$. In a particular embodiment, $R_3$ is —C(O)—$R_6$. In another particular embodiment, $R_3$ is S(O)$_2$—$R_{6a}$.

$R_3$ Taken Together with $R_5$

In a particular embodiment, $R_3$ taken together with $R_5$ is an optionally substituted imidazole ring of the formula:

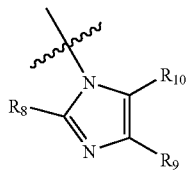

wherein $R_8$ is chosen from hydrogen, optionally substituted alkyl, optionally substituted aryl, optionally substituted aralkyl, optionally substituted heteroaralkyl, and optionally substituted heteroaryl; and $R_9$ and $R_{10}$ are independently hydrogen, optionally substituted alkyl, optionally substituted aryl, or optionally substituted aralkyl.

More particularly, $R_8$ is aryl (especially phenyl), substituted aryl (especially lower alkyl-, lower alkoxy-, and/or halo-substituted phenyl), aralkyl (especially benzyl and phenylvinyl), heteroaryl, substituted heteroaryl, heteroaralkyl, substituted aralkyl (especially substituted benzyl and substituted styrenyl), or substituted heteroaralkyl.

In another particular embodiment, $R_3$ taken together with $R_5$ is an optionally substituted imidazoline of the formula

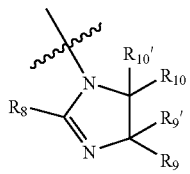

wherein, $R_8$ is chosen from hydrogen, optionally substituted alkyl, optionally substituted aryl, optionally substituted aralkyl, optionally substituted heteroaralkyl, and optionally substituted heteroaryl; and $R_9$, $R_{9'}$, $R_{10}$, and $R_{10'}$ are independently chosen from hydrogen, optionally substituted alkyl, optionally substituted aryl, and optionally substituted aralkyl.

More particularly, $R_8$ is aryl (especially phenyl), substituted aryl (especially lower alkyl-, lower alkoxy-, and/or halo-substituted phenyl), aralkyl (especially benzyl and phenylvinyl), heteroaryl, substituted heteroaryl, heteroaralkyl, substituted aralkyl (especially substituted benzyl and substituted styrenyl), or substituted heteroaralkyl.

In a most particular embodiment, $R_9$, $R_{9'}$, $R_{10}$, and $R_{10'}$ are independently selected from the group consisting of hydrogen and optionally substituted lower alkyl.

When considering the compounds of Formula I, in another embodiment, $R_3$ taken together with $R_5$ forms an optionally substituted diazepinone ring of the formula:

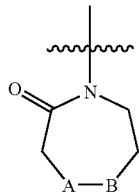

wherein A and B are each independently chosen from $C(R_{20})(R_{21})$, $N(R_{22})$, O or S, wherein $R_{20}$ and $R_{21}$ are each independently selected from H, optionally substituted alkyl optionally substituted aryl and optionally substituted heteroaryl; and $R_{22}$ is H, optionally substituted alkyl, optionally substituted aralkyl, optionally substituted heteroaralkyl, optionally substituted alkylcarbonyl, optionally substituted arylcarbonyl, optionally substituted heteroarylcarbonyl, optionally substituted aralkylcarbonyl, optionally substituted heteroaralkylcarbonyl, optionally substituted alkoxycarbonyl, optionally substituted aryloxycarbonyl, optionally substituted heteroaryloxycarbonyl, optionally substituted aralkyloxycarbonyl, optionally substituted heteroaralkyloxycarbonyl. In a more particular embodiment, the diazepinone ring is further substituted with one or more of the following groups: optionally substituted alkyl, optionally substituted aryl, optionally substituted aralkyl, optionally substituted heteroaryl, and optionally substituted heteroaralkyl.

In yet another embodiment of the compounds of Formula I, one of A or B is $C(R_{20})(R_{21})$, wherein $R_{20}$ and $R_{21}$ are each independently selected from H or $C_1$-$C_4$ alkyl, and the other of A or B is $N(R_{22})$, where $R_{22}$ is H, $C_1$-$C_4$ alkyl, optionally substituted aralkyl, optionally substituted heteroaralkyl, $C_1$-$C_6$ alkylcarbonyl, optionally substituted arylcarbonyl, optionally substituted heteroarylcarbonyl, optionally substituted aralkylcarbonyl, optionally substituted heteroaralkylcarbonyl, $C_1$-$C_6$ alkoxycarbonyl, optionally substituted aryloxycarbonyl, optionally substituted heteroaryloxycarbonyl, optionally substituted aralkyloxycarbonyl, optionally substituted heteroaralkyloxycarbonyl, where the optionally substituted aryl or heteroaryl groups or moieties are unsubstituted or substituted with one or more substituents selected from $C_1$-$C_4$ alkyl, $C_1$-$C_4$ haloalkyl, $C_1$-$C_4$ alkoxy, $C_1$-$C_4$ haloalkoxy, amino, $C_1$-$C_4$ alkylamino, di-$C_1$-$C_4$ alkylamino, carboxy, $C_1$-$C_4$ alkylcarbonyloxy, $C_1$-$C_4$ alkoxycarbonyl, carboxamido, $C_1$-$C_4$ alkylcarboxamido, aminocarbonyl, $C_1$-$C_4$ alkylaminocarbonyl, di-$C_1$-$C_4$ alkylaminocarbonyl, cyano, $C_1$-$C_4$ alkylcarbonyl, halogen, hydroxyl, mercapto and nitro. In another embodiment, A is $C(R_{20})(R_{21})$, wherein $R_{20}$ and $R_{21}$ are each H or $C_1$-$C_4$ alkyl, and B is $N(R_{22})$, where $R_{22}$ is H, $C_1$-$C_4$ alkyl, aralkyl, heteroaralkyl, $C_1$-$C_6$ alkylcarbonyl, arylcarbonyl, heteroarylcarbonyl. In specific embodiments of the compounds of Formula I, A is $CH_2$, and B is $N(R_{22})$, where $R_{22}$ is H, methyl, benzyl or acetyl(—C(O)methyl). See, e.g., U.S. Ser. No. 60/435,001, which is incorporated herein by reference for all purposes.

In another embodiment, $R_3$ taken together with $R_5$ forms an optionally substituted piperazine- or diazepam of the formula:

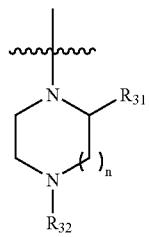

$R_{31}$ and $R_{32}$ are independently chosen from hydrogen, optionally substituted alkyl, optionally substituted aryl, optionally substituted heteroaryl, optionally substituted aralkyl, and optionally substituted heteroaralkyl; and n is 1 or 2. More particularly, $R_{31}$ is aryl (especially phenyl), substituted aryl (especially lower alkyl-, lower alkoxy-, and/or halo-substituted phenyl), aralkyl (especially benzyl and phenylvinyl), heteroaralkyl, substituted aralkyl (especially substituted benzyl and substituted phenylvinyl), or substituted heteroaralkyl; $R_{32}$ is hydrogen; and n is 1. See, e.g., U.S. Ser. No. 60/404,864, which is incorporated herein by reference.

$R_5$

When considering compounds of Formula I, in a particular embodiment, $R_5$ is chosen from hydrogen, optionally substituted $C_1$-$C_{13}$ alkyl, optionally substituted aryl, optionally substituted aryl-$C_1$-$C_4$-alkyl-, optionally substituted heterocyclyl, and optionally substituted heteroaryl-$C_1$-$C_4$-alkyl- (especially hydrogen or optionally substituted $C_1$-$C_{13}$ alkyl).

More particularly, $R_5$ is chosen from hydrogen, $C_1$-$C_4$ alkyl; cyclohexyl; phenyl substituted with hydroxyl, $C_1$-$C_4$ alkoxy or $C_1$-$C_4$ alkyl; benzyl; and $R_{11}$-alkylene-, wherein $R_{11}$ is hydroxyl, carboxy, ($C_1$-$C_4$ alkoxy)carbonyl-, di($C_1$-$C_4$ alkyl)amino-, ($C_1$-$C_4$ alkyl)amino-, amino, ($C_1$-$C_4$ alkoxy) carbonylamino-, $C_1$-$C_4$ alkoxy-, or optionally substituted N-heterocyclyl- (particularly azetidinyl, morpholinyl, pyridinyl, indolyl, furanyl, pyrrolidinyl, piperidinyl or imidazolyl, each of which may be otionally substituted).

In a particular embodiment, $R_5$ is chosen from hydrogen, methyl, ethyl, propyl, butyl, cyclohexyl, carboxyethyl, carboxymethyl, methoxyethyl, hydroxyethyl, hydroxypropyl, dimethylaminoethyl, dimethylaminopropyl, diethylaminoethyl, diethylaminopropyl, aminopropyl, methylaminopropyl, 2,2-dimethyl-3-(dimethylamino)propyl, aminoethyl, aminobutyl, aminopentyl, aminohexyl, isopropylaminopropyl, diisopropylaminoethyl, 1-methyl-4-(diethylamino)butyl, (t-Boc)aminopropyl, hydroxyphenyl, benzyl, methoxyphenyl, methylmethoxyphenyl, dimethylphenyl, tolyl, ethylphenyl, (oxopyrrolidinyl)propyl, (methoxycarbonyl)ethyl, benzylpiperidinyl, pyridinylethyl, pyridinylmethyl, morpholinylethyl morpholinylpropyl, piperidinyl, azetidinylmethyl, azetidinylethyl, azetidinylpropyl pyrrolidinylethyl, pyrrolidinylpropyl, piperidinylmethyl, piperidinylethyl, imidazolylpropyl, imidazolylethyl, (ethylpyrrolidinyl) methyl, (methylpyrrolidinyl)ethyl, (methylpiperidinyl) propyl, (methylpiperazinyl)propyl, furanylmethyl and indolylethyl.

In another embodiment, $R_5$ is $R_{11}$-alkylene-, wherein $R_{11}$ is amino, $C_1$-$C_4$ alkylamino-, di($C_1$-$C_4$ alkyl)amino-, $C_1$-$C_4$ alkoxy-, hydroxyl, or N-heterocyclyl. Particularly $R_{11}$ is amino. In a particular embodiment, the alkylene moiety of $R_{11}$-alkylene- has from 1 to 6 carbon atoms.

More particularly, $R_5$ is aminoethyl, aminopropyl, aminobutyl, aminopentyl, aminohexyl, methylaminoethyl, methylaminopropyl, methylaminobutyl, methylaminopentyl, methylaminohexyl, dimethylaminoethyl, dimethylaminopropyl, dimethylaminobutyl, dimethylaminopentyl, dimethylaminohexyl, ethylaminoethyl, ethylaminopropyl, ethylaminobutyl, ethylaminopentyl, ethylaminohexyl, diethylaminoethyl, diethylaminopropyl, diethylaminobutyyl, diethylaminopentyl, or diethylaminohexyl, most particularly aminopropyl.

$R_6$

When considering the compounds of Formula I, wherein $R_3$ is —C(O)$R_6$, in a particular embodiment, $R_6$ is selected from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, optionally substituted aryl, $R_7$O— and $R_{12}$—NH—, $R_7$ is chosen from optionally substituted $C_1$-$C_8$ alkyl and optionally substituted aryl, and $R_{12}$ is chosen from hydrogen, optionally substituted $C_1$-$C_8$ alkyl and optionally substituted aryl.

Particular $R_6$ are selected from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, and optionally substituted aryl. In a more particular embodiment, $R_6$ is chosen from phenyl;

phenyl substituted with one or more of the following substituents: halo; $C_1$-$C_4$ alkyl; $C_1$-$C_4$ alkyl substituted with hydroxy (e.g., hydroxymethyl); $C_1$-$C_4$ alkoxy; $C_1$-$C_4$ alkyl substituted with $C_1$-$C_4$ alkoxy, halo, nitro, formyl, carboxy, cyano, methylenedioxy, ethylenedioxy, acyl (e.g., acetyl), —N-alkyl (e.g., N-acetyl) or trifluoromethyl;

benzyl;

phenoxymethyl-;

halophenoxymethyl-;

phenylvinyl-;

heteroaryl-;

heteroaryl- substituted with $C_1$-$C_4$ alkyl or $C_1$-$C_4$ alkyl substituted with halo (e.g., $CF_3$);

$C_1$-$C_4$ alkyl substituted with $C_1$-$C_4$ alkoxy-; and benzyloxymethyl-.

In a most particular embodiment, when $R_6$ is not $R_{12}$NH— or $R_7$O—, $R_6$ is chosen from phenyl, halophenyl, dihalophenyl, cyanophenyl, halo(trifluoromethyl)phenyl, hydroxymethylphenyl, methoxymethylphenyl, methoxyphenyl, ethoxyphenyl, carboxyphenyl, formylphenyl, ethylphenyl, tolyl, methylenedioxyphenyl, ethylenedioxyphenyl, methoxychlorophenyl, dihydro-benzodioxinyl, methylhalophenyl, trifluoromethylphenyl, furanyl, $C_1$-$C_4$ alkyl substituted furanyl, trifluoromethylfuranyl, $C_1$-$C_4$ alkyl substituted trifluoromethylfuranyl, benzofuranyl, thiophenyl, $C_1$-$C_4$ alkyl substituted thiophenyl, benzothiophenyl, benzothiadiazolyl, pyridinyl, indolyl, methylpyridinyl, trifluoromethylpyridinyl, pyrrolyl, quinolinyl, picolinyl, pyrazolyl, $C_1$-$C_4$ alkyl substituted pyrazolyl, N-methylpyrazolyl, $C_1$-$C_4$ alkyl substituted N-methyl pyrazolyl, $C_1$-$C_4$ alkyl substituted pyrazinyl, $C_1$-$C_4$ alkyl substituted isoxazolyl, benzoisoxazolyl, morpholinomethyl, methylthiomethyl, methoxymethyl, N-methyl imidazolyl, and imidazolyl. Yet more particularly, $R_6$ is optionally substituted phenyl (especially, tolyl, halophenyl, methylhalophenyl, hydroxymethylphenyl, halo(trifluoromethyl)phenyl-, methylenedioxyphenyl, formylphenyl or cyanophenyl).

In a more particular embodiment, when $R_6$ is $R_{12}$NH—, $R_{12}$ is chosen from hydrogen, $C_1$-$C_4$ alkyl; cyclohexyl; phenyl; and phenyl substituted with halo, $C_1$-$C_4$ alkyl, trifluoromethyl, $C_1$-$C_4$ alkoxy, or $C_1$-$C_4$ alkylthio.

In a most particular embodiment, when $R_6$ is $R_{12}$NH—, $R_{12}$ is hydrogen isopropyl, butyl, cyclohexyl, phenyl, bromophenyl, dichlorophenyl, methoxyphenyl, ethylphenyl, tolyl, trifluoromethylphenyl or methylthiophenyl.

In an embodiment, wherein $R_6$ is $R_7$O—, $R_7$ is chosen from optionally substituted $C_1$-$C_8$ alkyl and optionally substituted aryl.

$R_{6a}$

In a particular embodiment, $R_{6a}$ is chosen from $C_1$-$C_{13}$ alkyl; phenyl; naphthyl; phenyl substituted with halo, lower alkyl, lower alkoxy, nitro, methylenedioxy, or trifluoromethyl; biphenylyl and heteroaryl. More particularly, $R_{6a}$ is chosen from substituted phenyl and naphthyl.

Salt Forms

Compounds of the invention will generally be capable of forming acid addition salts (i.e., will comprise a site which reacts with a pharmaceutically acceptable acid to form an acid addition salt.) The present invention includes pharmaceutically acceptable acid addition salts of the compounds of Formula I. Acid addition salts of the present compounds are prepared in a standard manner in a suitable solvent from the parent compound and an excess of an acid, such as hydrochloric, hydrobromic, sulfuric, phosphoric, acetic, maleic, succinic or methanesulfonic.

The salts and/or solvates of the compounds of the Formula I which are not pharmaceutically acceptable may be useful as intermediates in the preparation of pharmaceutically acceptable salts and/or solvates of compounds of Formula I or the compounds of the Formula I themselves, and as such form another aspect of the present invention.

Particular Subgenus

In a particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; $R_3$ is hydrogen; and $R_5$ is hydrogen.

In another particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; 4 is optionally substituted methyl or optionally substituted phenyl; and $R_3$ is —C(O)$R_6$; $R_6$ is optionally substituted phenyl (especially, tolyl, halophenyl, methylhalophenyl, hydroxymethylphenyl, halo(trifluoromethyl)phenyl-, methylenedioxyphenyl, formylphenyl or cyanophenyl); and $R_5$ is optionally substituted alkyl (particularly where $R_5$ is $R_{11}$-alkylene- wherein $R_{11}$ is amino, $C_1$-$C_4$ alkylamino-, di($C_1$-$C_4$ alkyl)amino-, $C_1$-$C_4$ alkoxy-, hydroxyl, or N-heterocyclyl).

In another particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; $R_3$ is chosen from optionally substituted $C_1$-$C_{13}$ alkyl (especially substituted $C_1$-$C_4$ alkyl); optionally substituted aralkyl (especially optionally substituted benzyl or maphthylmethyl-); and optionally substituted heteroaralkyl; and $R_5$ is optionally substituted alkyl (particularly where $R_5$ is $R_{11}$-alkylene- wherein $R_{11}$ is amino, $C_1$-$C_4$ alkylamino-, di($C_1$-$C_4$ alkyl)amino-, $C_1$-$C_4$ alkoxy-, hydroxyl, or N-heterocyclyl).

In a particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; and $R_3$ and $R_5$ taken together form an optionally substituted imidazolinyl ring.

In a particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; and $R_3$ taken together with $R_5$ form an optionally substituted imidazolyl ring.

In a particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; and $R_3$ and $R_5$ taken together form an optionally substituted imidazolidinyl ring.

In a particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; and $R_3$ and $R_5$ taken together form an optionally substituted piperazinyl ring.

In a particular subgenus of compounds of Formula I, T and T' are absent; $R_1$ is benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; and $R_3$ and $R_5$ taken together form an optionally substituted diazepinoyl ring.

In a particular subgenus of compounds of Formula I, T and T' are absent; $R_1$ is most preferably chosen from benzyl, halobenzyl, methylbenzyl, methoxylbenzyl, cyanobenzyl, hydroxybenzyl, or naphthylmethyl; $R_2$ is optionally substituted $C_1$-$C_4$ alkyl; $R_{2'}$ is hydrogen; $R_4$ is optionally substituted methyl or optionally substituted phenyl; $R_5$ is optionally substituted alkyl (particularly where $R_5$ is $R_{11}$-alkylene- wherein $R_{11}$ is amino, carboxy, hydroxy, di(lower alkylamino), (lower alkyl)amino, lower alkoxy, or N-heterocyclyl (especially pyrrolidino, piperidino, azetidino, imidzolyl, or morpholino)), $R_3$ is —SO$_2$$R_{6a}$, and $R_{6a}$ is substituted phenyl or naphthyl.

Particular compounds include:

N-(3-amino-propyl)-N-[1-(4-benzyl-6-methyl-5-oxo-4,5-dihydro-[1,2,4]triazin-3-yl)-2-methyl-propyl]-4-methyl-benzamide; and 4-benzyl-3-[1-(2-methyl-imidazol-1-yl)-propyl]-4H-[1,2,4]triazin-5-one.

Utility, Testing and Administration

General Utility

Once made, the compounds of the invention find use in a variety of applications involving alteration of mitosis. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In a particular embodiment, the compounds of the invention are used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest and monopolar spindle formation.

The compounds of the invention are useful to bind to, and/or inhibit the activity of, a mitotic kinesin, KSP. In one embodiment, the KSP is human KSP, although the compounds may be used to bind to or inhibit the activity of KSP kinesins from other organisms. In this context, "inhibit" means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See U.S. Pat. No. 6,437,115, hereby incorporated by reference in its entirety. The compounds of the invention have been shown to have specificity for KSP. However, the present invention includes the use of the compounds to bind to or modulate other mitotic kinesins.

The compounds of the invention are used to treat cellular proliferation diseases. Such disease states which can be treated by the compounds, compositions and methods provided herein include, but are not limited to, cancer (further discussed below), autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in one embodiment, the invention herein includes application to cells or individuals afflicted or subject to impending affliction with any one of these disorders or states.

The compounds, pharmaceutical formulations and methods provided herein are particularly deemed useful for the treatment of cancer including solid tumors such as skin, breast, brain, cervical carcinomas, testicular carcinomas, etc. More particularly, cancers that can be treated include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

As used herein, treatment of cancer includes treatment of cancerous cells, including cells afflicted by any one of the above-identified conditions. Thus, the term "cancerous cell" as provided herein, includes a cell afflicted by any one of the above identified conditions.

Another useful aspect of the invention is a kit having a compound, salt or solvate of Formula I and a package insert or other labeling including directions treating a cellular proliferative disease by administering an effective amount of the compound, salt or solvate. The compound, salt or solvate of Formula I in the kits of the invention is particularly provided as one or more doses for a course of treatment for a cellular proliferative disease, each dose being a pharmaceutical formulation including a pharmaceutically accepted excipient and a compound, salt or solvate of Formula I.

Testing

For assay of KSP-modulating activity, generally either KSP or a compound according to the invention is non-diffusably bound to an insoluble support having isolated sample receiving areas (e.g., a microtiter plate, an array, etc.). The insoluble support may be made of any composition to which the sample can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the sample is not crucial so long as it is compatible with the reagents and overall methods of the invention, maintains the activity of the sample and is nondiffusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the sample, excess unbound material is removed by washing. The sample receiving areas may then be blocked through incubation with bovine serum albumin (BSA), casein or other innocuous protein or other moiety.

The compounds of the invention may be used on their own to inhibit the activity of a mitotic kinesin, particularly KSP. In one embodiment, a compound of the invention is combined with KSP and the activity of KSP is assayed. Kinesin (including KSP) activity is known in the art and includes one or more kinesin activities. Kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. (See e.g., Hall, et al. (1996), Biophys. J., 71: 3467-3476, Turner et al., 1996, AnaL. Biochem. 242 (1):20-5; Gittes et al., 1996, Biophys. J. 70(1): 418-29; Shirakawa et al., 1995, J. Exp. BioL. 198: 1809-15; Winkelmann et al., 1995, Biophys. J. 68: 2444-53; Winkelmann et al., 1995, Biophys. J. 68: 72S.)

Methods known in the art for determining ATPase hydrolysis activity also can be used. Suitably, solution based assays are utilized. U.S. Pat. No. 6,410,254, hereby incorporated by reference in its entirety, describes such assays. Alternatively, conventional methods are used. For example, $P_i$ release from kinesin can be quantified. In one embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 μL of the reaction mixture is quenched in 90 μL of cold 0.3 M PCA. Phosphate standards are used so data can be converted to mM inorganic phosphate released. When all reactions and standards have been quenched in PCA, 100 μL of malachite green reagent is added to the relevant wells in e.g., a microtiter plate. The mixture is developed for 10-15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of agents and are well known to those skilled in the art. In one embodiment ATPase assays of kinesin are performed in the absence of microtubules. In another embodiment, the ATPase assays are performed in the presence of microtubules. Different types of agents can be detected in the above assays. In a one embodiment, the effect of an agent is independent of the concentration of microtubules and ATP. In another embodiment, the effect of the agents on kinesin ATPase can be decreased by increasing the concentrations of ATP, microtubules or both. In yet another embodiment, the effect of the agent is increased by increasing concentrations of ATP, microtubules or both.

Compounds that inhibit the biochemical activity of KSP in vitro may then be screened in vivo. In vivo screening methods include assays of cell cycle distribution, cell viability, or the presence, morphology, activity, distribution, or number of mitotic spindles. Methods for monitoring cell cycle distribution of a cell population, for example, by flow cytometry, are well known to those skilled in the art, as are methods for determining cell viability. See for example, U.S. Pat. No. 6,437,115, hereby incorporated by reference in its entirety. Microscopic methods for monitoring spindle formation and malformation are well known to those of skill in the art (see, e.g., Whitehead and Rattner (1998), J. Cell Sci. 111:2551-61; Galgio et al, (1996) J. Cell Biol., 135:399-414), each incorporated herein by reference in its entirety.

The compounds of the invention inhibit the KSP kinesin. One measure of inhibition is $IC_{50}$, defined as the concentration of the compound at which the activity of KSP is decreased by fifty percent relative to a control. Preferred compounds have $IC_{50}$'s of less than about 1 mM, with preferred embodiments having $IC_{50}$'s of less than about 100 μM, with more preferred embodiments having $IC_{50}$'s of less than about 10 μM, with particularly preferred embodiments having $IC_{50}$'s of less than about 1 μM, and especially preferred embodiments having $IC_{50}$'s of less than about 100 nM, and with the most preferred embodiments having $IC_{50}$'s of less than about 10 nM. Measurement of $IC_{50}$ is done using an ATPase assay such as described herein.

Another measure of inhibition is $K_i$. For compounds with $IC_{50}$'s less than 1 μM, the $K_i$ or $K_d$ is defined as the dissociation rate constant for the interaction of the compounds described herein with KSP. Preferred compounds have $K_i$'s of less than about 100 μM, with preferred embodiments having $K_i$'s of less than about 10 μM, and particularly preferred embodiments having $K_i$'s of less than about 1 μM and especially preferred embodiments having $K_i$'s of less than about 100 nM, and with the most preferred embodiments having $K_i$'s of less than about 10 nM.

The $K_i$ for a compound is determined from the $IC_{50}$ based on three assumptions and the Michaelis-Menten equation. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Preferred compounds have $GI_{50}$'s of less than about 1 mM; those having a $GI_{50}$ of less than about 20 μM are more preferred; those having a $GI_{50}$ of less than about 10 μM more so; those having a $GI_{50}$ of less than about 1 μM more so; those having a $GI_{50}$ of less than about 100 nM more so; and those having a $GI_{50}$ of less than about 10 nM even more so. Measurement of $GI_{50}$ is done using a cell proliferation assay such as described herein. Compounds of this class were found to inhibit cell proliferation.

In vitro potency of small molecule inhibitors is determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation, irrespective of the concentration demonstrating inhibition, have potential clinical usefulness.

To employ the compounds of the invention in a method of screening for compounds that bind to KSP kinesin, the KSP is bound to a support, and a compound of the invention is added to the assay. Alternatively, the compound of the invention is bound to the support and KSP is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the compound of the invention to KSP may be done in a number of ways. In one embodiment, the compound is labeled, for example, with a fluorescent or radioactive moiety, and binding is determined directly. For example, this may be done by attaching all or a portion of KSP to a solid support, adding a labeled test compound (for example a compound of the invention in which at least one atom has been replaced by a detectable isotope), washing off excess reagent, and determining whether the amount of the label is that present on the solid support.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}I$ or with fluorophores. Alternatively, more than one component may be labeled with different labels; using $^{125}I$ for the proteins, for example, and a fluorophor for the antimitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that particular protein, for example, polymer structures such as microtubules, and energy sources such as ATP. Particular embodiments of assays herein include candidate agents which do not bind the cellular proliferation protein in its endogenous native state termed herein as "exogenous" agents. In another embodiment, exogenous agents further exclude antibodies to KSP.

Candidate agents can encompass numerous chemical classes, though typically they are organic molecules, preferably they are small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl-, hydroxyl-, ether, or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, and/or amidification to produce structural analogs.

Competitive screening assays may be done by combining KSP and a drug candidate in a first sample. A second sample comprises a compound of the present invention, KSP and a drug candidate. This may be performed in either the presence or absence of microtubules. The binding of the drug candidate is determined for both samples, and a change, or difference in binding between the two samples indicates the presence of a drug candidate capable of binding to KSP and potentially inhibiting its activity. That is, if the binding of the drug candidate is different in the second sample relative to the first sample, the drug candidate is capable of binding to KSP.

In a particular embodiment, the binding of the candidate agent to KSP is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations may be performed at any temperature which facilitates optimal activity, typically between 4 and 40° C.

Incubation periods are selected for optimum activity, but may also be optimized to facilitate rapid high throughput screening. Typically between 0.1 and 1 hour will be sufficient. Excess reagent is generally removed or washed away.

The second component is then added, and the presence or absence of the labeled component is followed, to indicate binding.

In another embodiment, the competitor is added first, followed by the candidate agent. Displacement of the competitor is an indication the candidate agent is binding to KSP and thus is capable of binding to, and potentially inhibiting, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

Inhibition is tested by screening for candidate agents capable of inhibiting the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Suitably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Administration

Accordingly, the compounds of the invention are administered to cells. By "administered" herein is meant administration of a therapeutically effective dose of a compound of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered.

A "patient" for the purposes of the present invention includes both humans and other animals, particularly mammals, and other organisms. Thus the methods are applicable to both human therapy and veterinary applications. In the preferred embodiment the patient is a mammal, and in the most preferred embodiment the patient is human.

Compounds of the invention having the desired pharmacological activity may be administered, preferably as a pharmaceutically acceptable composition comprising an pharmaceutical excipient, to a patient, as described herein. Depending upon the manner of introduction, the compounds may be formulated in a variety of ways as discussed below. The concentration of therapeutically active compound in the formulation may vary from about 0.1-100 wt. %.

The agents may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of a compound of the present invention. In one aspect of the invention, a compound of the present invention is co-administered with one or more other chemotherapeutic agents. By "co-administer" it is meant that the present compounds are administered to a patient such that the present compounds as well as the co-administered compound may be found in the patient's bloodstream at the same time, regardless when the compounds are actually administered, including simultaneously.

The administration of the compounds and compositions of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical dosage forms include a compound of formula I or a pharmaceutically acceptable salt, solvate, or solvate of a salt thereof, and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated. Such fluids are prepared with water for injection USP.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:

- alcohol, e.g., 5% alcohol (e.g., in dextrose and water ("D/W") or D/W in normal saline solution ("NSS"), including in 5% dextrose and water ("D5/W"), or D5/W in NSS);
- synthetic amino acid such as Aminosyn, FreAmine, Travasol, e.g., 3.5 or 7; 8.5; 3.5, 5.5 or 8.5% respectively;
- ammonium chloride e.g., 2.14%;
- dextran 40, in NSS e.g., 10% or in D5/W e.g., 10%;
- dextran 70, in NSS e.g., 6% or in D5/W e.g., 6%;
- dextrose (glucose, D5/W) e.g., 2.5-50%;
- dextrose and sodium chloride e.g., 5-20% dextrose and 0.22-0.9% NaCl;
- lactated Ringer's (Hartmann's) e.g., NaCl 0.6%, KCl 0.03%, CaCl$_2$ 0.02%;
- lactate 0.3%;
- mannitol e.g., 5%, optionally in combination with dextrose e.g., 10% or NaCl e.g., 15 or 20%;
- multiple electrolyte solutions with varying combinations of electrolytes, dextrose, fructose, invert sugar Ringer's e.g., NaCl 0.86%, KCl 0.03%, CaCl$_2$ 0.033%;
- sodium bicarbonate e.g., 5%;
- sodium chloride e.g., 0.45, 0.9, 3, or 5%;
- sodium lactate e.g., ⅙ M; and
- sterile water for injection The pH of such IV fluids may vary, and will typically be from 3.5 to 8 as known in the art.

The compounds, pharmaceutically acceptable salts and solvates of the invention can be administered alone or in combination with other treatments, i.e., radiation, or other therapeutic agents, such as the taxane class of agents that appear to act on microtubule formation or the camptothecin class of topoisomerase I inhibitors. When so-used, other therapeutic agents can be administered before, concurrently (whether in separate dosage forms or in a combined dosage form), or after administration of an active agent of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All publications, including but not limited to patents and patent applications, cited in this specification are herein incorporated by reference as if each individual publication were specifically and individually indicated to be incorporated by reference herein as though fully set forth.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

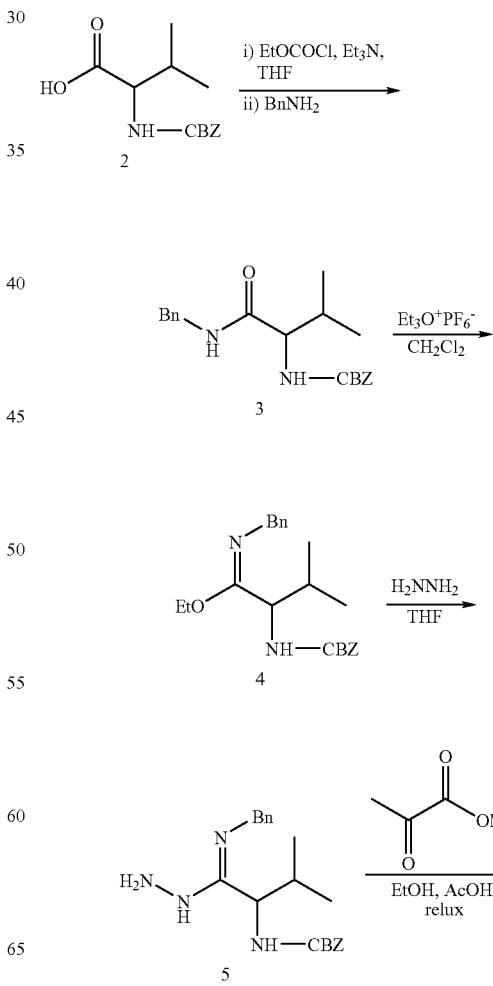

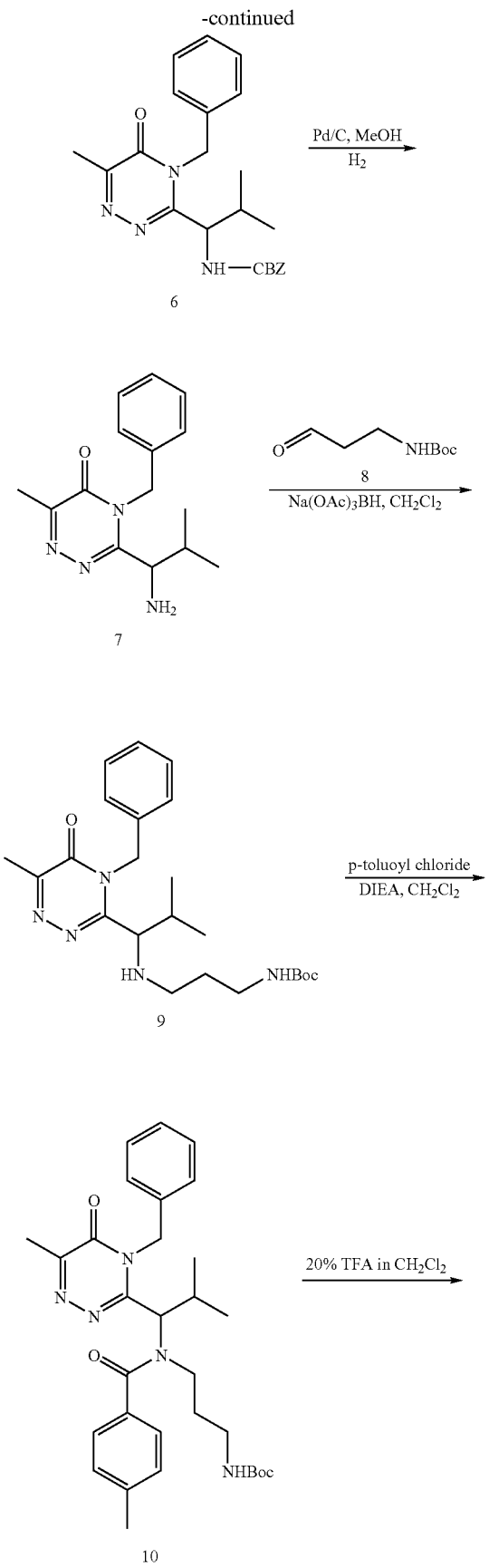

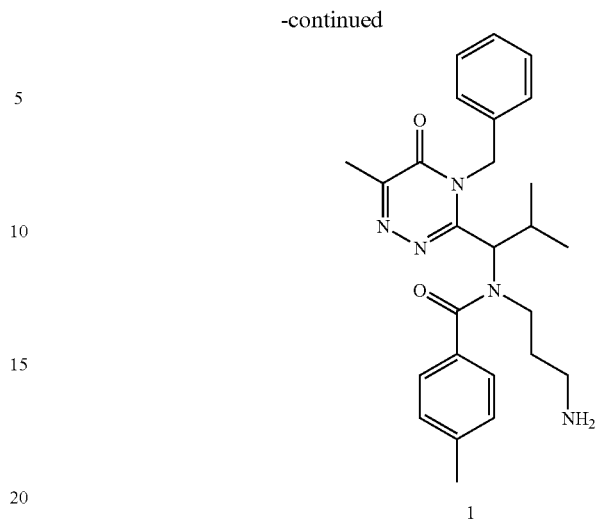

To a solution of CBZ-Valine (2, 50 g, 200 mmol) in THF (700 mL) were added ethyl chloroformate (23 mL, 240 mmol) and triethylamine (33.5 mL, 240 mmol) at 0° C. The reaction mixture was stirred under nitrogen. After 1 hour, benzylamine (26.2 mL, 240 mmol) was added over 5 minutes. Upon completion of addition, the reaction solution was allowed to warm to room temperature. After 1 hour, the reaction mixture was filtered. The precipitate was washed with water and THF, and dried in vacuo to give 3 (60 g, 88%) as a white solid. LRMS (M+H$^+$) m/z 341.1.

To a suspension of 3 (20 g, 59 mmol) in dichloromethane (500 mL) was added triethyloxonium hexafluorophosphate (25 g, 100 mmol). The resulting mixture was stirred for 14 hours. The reaction mixture was washed with saturated NaHCO$_3$ and brine, dried over Na$_2$SO$_4$, and concentrated to give 4 (19 g), which was used in the next step without further purification. LRMS (M+H$^+$) m/z 369.1.

To a solution of above crude 4 (4 g, ~10.85 mmol) in THF (30 mL) was added hydrazine (1.0 M in THF, 20 mL). The resulting mixture was stirred for 4 hours. The solution was concentrated and dried in vacuo to give 5 (3.8 g) as a pale-yellow solid, which was used in the next step without further purification. LRMS (M+H$^+$) m/z 355.1.

A solution of above crude 5 (3.5 g, ~9.85 mmol) and methyl pyruvate (1.4 mL, 15 mmol) in EtOH was refluxed for 4 hours. AcOH (800 µL) was added. Refluxing continued for additional 6 hours. The reaction mixture was concentrated. The resulting residue was purified via flash column chromatography using a mixture of ethyl acetate and hexane as eluent to give 6 (1.0 g, 24% from 3) as a white solid. LRMS (M+H$^+$) m/z 407.1.

A solution of 6 (500 mg, 1.23 mmol) in MeOH (20 mL) was stirred under a stream of H$_2$ (30 psi) in the presence of 10% Pd/C (50 mg) for 40 minutes. The catalyst was removed by filtration through a PTFE (0.45 um) filter and the solvent evaporated to give 7 (400 mg), which was used in the next step without further purification. LRMS (M+H$^+$) m/z 273.1.

To a solution of above crude 7 (400 mg, ~1.47 mmol) in dichloromethane (35 mL) at 0° C. was added aldehyde 8 (330 mg, 1.91 mmol) and sodium triacetoxyborohydride (406 mg, 1.91 mmol), successively. The resulting mixture was stirred under nitrogen for 14 hours, followed by addition of saturated NaHCO$_3$ (20 mL). The organic layer was separated, and the aqueous phase was extracted with dichloromethane (2×50 mL). The combined organic layers were washed with brine, dried over $Na_2SO_4$, and concentrated to give 9 (700 mg) as a yellow oil, which was used in the next step without further purification. LRMS (M+H$^+$) m/z 430.2.

To a solution of above crude 9 (350 mg, 0.82 mmol) and N,N-diisopropylethylamine (242 µL, 1.39 mmol) in dichloromethane (12 mL) at 0° C. was added p-toluoyl chloride (183 µL, 1.39 mmol). The resulting solution was stirred under nitrogen at room temperature for 20 hours. The solution was concentrated. The resulting residue was purified on RP-HPLC using a mixture of acetonitrile and $H_2O$ to give 9 (80 mg, 36% from 6). LRMS (M+H$^+$) m/z 548.2.

To a solution of 10 (40 mg, 0.073 mmol) in dichloromethane (4 mL) was added trifluoroacetic acid (1 mL). The resulting solution was stirred at room temperature for 1 hour and then concentrated under reduced pressure. The residue was dried under high vacuum and dissolved in dichloromethane (15 mL). It was washed with saturated $NaHCO_3$ (15 mL), and the aqueous phase was extracted with dichloromethane (2×25 mL). The combined organic layers were dried over $Na_2SO_4$, and concentrated to give 1 (20 mg, 62%) as a white solid, which was fully characterized with $^1$H-NMR and LC/MS analysis (LRMS (M+H$^+$) m/z 448.2)

Example 2

Inhibition of Cellular Viability in Tumor Cell Lines Treated with KSP Inhibitors.

Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 µM.

Procedure: Day 1—Cell Plating:
Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/100 µL) is added to all wells of 96-well plates, followed by incubation for 18 to 24 hours at 37° C., 100% humidity, and 5% $CO_2$ allowing the cells to adhere to the plates.

Procedure: Day 2—Compound Addition:
To one column of the wells of an autoclaved assay block are added an initial 2.5 µL of test compound(s) at 400× the highest desired concentration. 1.25 µL of 400× (400 µM) Topotecan is added to other wells (ODs from these wells are used to subtract out for background absorbance of dead cells and vehicle). 500 µL of media without DMSO are added to the wells containing test compound, and 250 µL to the Topotecan wells. 250 µL of media+0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading:
The plates are removed from the incubator and 40 µl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis
The normalized % of control (absorbance-background) is calculated and an XLfit is used to generate a dose-response curve from which the concentration of compound required to inhibit viability by 50% is determined. The compounds of the present invention show activity when tested by this method.

Example 3

Monopolar Spindle Formation following Application of a KSP Inhibitor

Human tumor cells Skov-3 (ovarian) were plated in 96-well plates at densities of 4,000 cells per well, allowed to adhere for 24 hours, and treated with various concentrations of the test compounds for 24 hours. Cells were fixed in 4% formaldehyde and stained with antitubulin antibodies (subsequently recognized using fluorescently-labeled secondary antibody) and Hoechst dye (which stains DNA).

Visual inspection revealed that the compounds caused cell cycle arrest in the prometaphase stage of mitosis. DNA was condensed and spindle formation had initiated, but arrested cells uniformly displayed monopolar spindles, indicating that there was an inhibition of spindle pole body separation. Microinjection of anti-KSP antibodies also causes mitotic arrest with arrested cells displaying monopolar spindles.

Example 4

Inhibition of Cellular Proliferation in Tumor Cell Lines Treated with KSP Inhibitors.

Cells were plated in 96-well plates at densities from 1000-2500 cells/well of a 96-well plate and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (I.S> U.S. Pat. No. 5,185,450) (see Promega product catalog #G3580, CellTiter 96® AQ$_{ueous}$ One Solution Cell Proliferation Assay) was used to determine the number of viable cells at $T_0$ and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this. KSP inhibitors inhibited cell proliferation in human ovarian tumor cell lines (SKOV-3).

A Gi$_{50}$ was calculated by plotting the concentration of compound in µM vs the percentage of cell growth of cell growth in treated wells. The Gi$_{50}$ calculated for the compounds is the estimated concentration at which growth is inhibited by 50% compared to control, i.e., the concentration at which:

$$100 \times [(\text{Treated}_{48} - T_0)/(\text{Control}_{48} - T_0)] = 50.$$

All concentrations of compounds are tested in duplicate and controls are averaged over 12 wells. A very similar 96-well plate layout and Gi$_{50}$ calculation scheme is used by the National Cancer Institute (see Monks, et al., J. Natl.

Cancer Inst. 83:757-766 (1991)). However, the method by which the National Cancer Institute quantitates cell number does not use MTS, but instead employs alternative methods.

Example 5

Calculation of $IC_{50}$:

Measurement of a composition's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 µM paclitaxel (Sigma T-7402), 10 ppm antifoam 289 (Sigma A-8436), 25 mM Pipes/KOH pH 6.8 (Sigma P6757), 2 mM MgC12 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM KSP motor domain, 50 µg/ml microtubules, 1 mM DTT (Sigma D9779), 5 µM paclitaxel (Sigma T-7402), 10 ppm antifoam 289 (Sigma A-8436), 25 mM Pipes/KOH pH 6.8 (Sigma P6757), 2 mM MgC12 (VWR JT4003-01), and 1 mM EGTA (Sigma E3889). Serial dilutions (8-12 two-fold dilutions) of the composition are made in a 96-well microtiter plate (Corning Costar 3695) using Solution 1. Following serial dilution each well has 50 µl of Solution 1. The reaction is started by adding 50 µl of solution 2 to each well. This may be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{Range}{1+\left(\frac{x}{IC_{50}}\right)^s} + Background$$

where y is the observed rate and x the compound concentration.

Other compounds of this class were found to inhibit cell proliferation, although $GI_{50}$ values varied. $GI_{50}$ values for the compounds tested ranged from 200 nM to greater than the highest concentration tested. By this we mean that although most of the compounds that inhibited KSP activity biochemically did inhibit cell proliferation, for some, at the highest concentration tested (generally about 20 µM), cell growth was inhibited less than 50%. Many of the compounds have $GI_{50}$ values less than 10 µM, and several have $GI_{50}$ values less than 1 µM. Anti-proliferative compounds that have been successfully applied in the clinic to treatment of cancer (cancer chemotherapeutics) have $GI_{50}$'S that vary greatly. For example, in A549 cells, paclitaxel G150 is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation at virtually any concentration may be useful. However, preferably, compounds will have $GI_{50}$ values of less than 1 mM. More preferably, compounds will have $GI_{50}$ values of less than 20 µM. Even more preferably, compounds will have $GI_{50}$ values of less than 10 µM. Further reduction in $GI_{50}$ values may also be desirable, including compounds with $GI_{50}$ values of less than 1 µM. Some of the compounds of the invention inhibit cell proliferation with $GI_{50}$ values from below 200 nM to below 10 nM.

All anhydrous solvents were purchased from Aldrich chemical company in SureSeal® containers. Most reagents were purchased from Aldrich Chemical Company. Reagents were added and aqueous extractions performed with single or multichannel pipettors. Filtrations were performed using Whatman/Polyfiltronics 24 well, 10 mL filtration blocks. Evaporation of volatile materials from the array was performed with a Labconco

What is claimed is:

1. A compound selected from the group represented by Formula I:

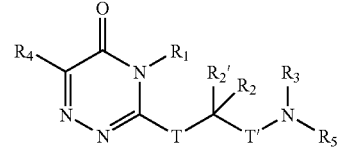

Formula I wherein:

T and T' are independently a covalent bond or optionally substituted lower alkylene;

$R_1$ is chosen from hydrogen, optionally substituted alkyl, optionally substituted aryl, optionally substituted aralkyl, optionally substituted heteroaryl, and optionally substituted heteroaralkyl;

$R_2$ and $R_2'$ are independently chosen from hydrogen, optionally substituted alkyl, optionally substituted aryl, optionally substituted aralkyl, optionally substituted heteroaryl, and optionally substituted heteroaralkyl; or $R_2$ and $R_2'$ taken together form an optionally substituted 3- to 7-membered ring;

$R_3$ is chosen from hydrogen, optionally substituted alkyl-, optionally substituted aryl-, optionally substituted aralkyl-, optionally substituted heteroaryl-, optionally substituted heteroaralkyl-, optionally substituted heterocyclyl-, —C(O)—$R_6$, and —S(O)$_2$—$R_{6a}$;

$R_5$ is chosen from hydrogen, optionally substituted alkyl-, optionally substituted aryl-, optionally substituted aralkyl-, optionally substituted heteroaralkyl-, and optionally substituted heterocyclyl-;

$R_6$ is chosen from hydrogen, optionally substituted alkyl, optionally substituted aryl, optionally substituted aralkyl, optionally substituted heteroaryl, optionally substituted heteroaralkyl, $R_7O$— and $R_{12}$—NH—;

$R_{6a}$ is chosen from optionally substituted alkyl, optionally substituted aryl, optionally substituted aralkyl, optionally substituted heteroaryl, optionally substituted heteroaralkyl, and $R_{12}$—NH—;

or $R_5$ taken together with $R_3$, and the nitrogen to which they are bound, form an optionally substituted 5- to 12-membered nitrogen-containing heterocycle, which optionally incorporates from one to two additional heteroatoms, selected from N, O, and S in the heterocycle ring;

or $R_5$ taken together with $R_2$ form an optionally substituted 5- to 12-membered nitrogen-containing heterocycle, which optionally incorporates from one to two additional heteroatoms, selected from N, O, and S in the heterocycle ring;

$R_7$ is chosen from optionally substituted alkyl, optionally substituted aryl, optionally substituted aralkyl, optionally substituted heteroaryl, and optionally substituted heteroaralkyl;

$R_{12}$ is chosen from hydrogen, optionally substituted alkyl, optionally substituted aryl, optionally substituted aralkyl, optionally substituted heteroaryl, and optionally substituted heteroaralkyl; and $R_4$ is chosen from hydrogen, optionally substituted alkyl, optionally substituted alkoxy, halogen, hydroxyl, nitro, cyano, optionally substituted amino, alkylsulfonyl, alkylsulfonamido, alkylthio, carboxyalkyl, aminocarbonyl, aryloxy, heteroaryloxy, optionally substituted N-heterocyclyl, optionally substituted aryl, optionally substituted aralkyl, optionally substituted heteroaralkyl and optionally substituted heteroaryl; or a pharmaceutically acceptable salt of a compound of Formula I.

2. The compound of claim 1 comprising one or more of the following:

T and T' are each a covalent bond;

$R_1$ is selected from hydrogen, optionally substituted $C_1$-$C_4$ alkyl, optionally substituted phenyl-$C_1$-$C_4$-alkyl-, optionally substituted naphthylmethyl, optionally substituted phenyl, and naphthyl;

$R_2$ is optionally substituted $C_1$-$C_4$ alkyl;

$R_{2'}$ is hydrogen or optionally substituted $C_1$-$C_4$ alkyl;

$R_3$ is —C(O)—$R_6$ or S(O)2—$R_{6a}$;

$R_4$ is hydrogen, halo, hydroxyl, optionally substituted lower alkyl, optionally substituted aryl, alkoxy, cyano, substituted amino, carbamyl, aryloxy, heteroaryloxy, heteroaryl, or optionally substituted N-heterocyclyl;

$R_6$ is selected from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, optionally substituted aryl, $R_7$O— and $R_{12}$—NH—, $R_{6a}$ is selected from $C_1$-$C_{13}$ alkyl; phenyl; naphthyl; phenyl substituted with halo, lower alkyl, lower alkoxy, nitro, methylenedioxy, or trifluoromethyl; biphenylyl and heteroaryl;

$R_7$ is chosen from optionally substituted alkyl and optionally substituted aryl;

$R_{12}$ is chosen from optionally substituted alkyl and optionally substituted aryl; and $R_5$ is chosen from hydrogen, optionally substituted $C_1$-$C_{13}$ alkyl, optionally substituted aryl, optionally substituted aryl-$C_1$-$C_4$-alkyl-, optionally substituted heterocyclyl, and optionally substituted heteroaryl-$C_1$-$C_4$-alkyl-.

3. The compound of claim 2 comprising one or more of the following:

$R_1$ is naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, chlorobenzyl, methylbenzyl, methoxybenzyl, cyanobenzyl, hydroxybenzyl, dichlorobenzyl, dimethoxybenzyl, or naphthylmethyl;

$R_{2'}$ is hydrogen;

$R_2$ is optionally substituted $C_1$-$C_4$ alkyl;

$R_3$ is —C(O)$R_6$;

$R_6$ is chosen from phenyl; substituted phenyl; benzyl; phenoxymethyl-; halophenoxymethyl-; phenylvinyl-; heteroaryl-; substituted heteroaryl-; $C_1$-$C_4$alkyl substituted with $C_1$-$C_4$ alkoxy-; and benzyloxymethyl-;

$R_4$ is chosen from hydrogen, hydroxyl, halo, optionally substituted lower alkyl, lower alkoxy, optionally substituted phenyl, and cyano;

$R_5$ is selected from hydrogen, $C_1$-$C_4$ alkyl; cyclohexyl; phenyl substituted with hydroxyl, $C_1$-$C_4$ alkoxy or $C_1$-$C_4$ alkyl; benzyl; and $R_{11}$-alkylene-; and $R_{11}$ is hydroxyl, carboxy, ($C_1$-$C_4$alkoxy)carbonyl-, di($C_1$-$C_4$alkyl)amino-, ($C_1$-$C_4$ alkyl)amino-, amino, ($C_1$-$C_4$ alkoxy)carbonylamino-, $C_1$-$C_4$ alkoxy-, or optionally substituted N-heterocyclyl-.

4. The compound of claim 3 comprising one or more of the following:

$R_1$ is benzyl, halobenzyl, methylbenzyl, methoxybenzyl, cyanobenzyl, hydroxybenzyl, or naphthylmethyl;

$R_2$ is chosen from methyl, ethyl, propyl, butyl, methylthioethyl, methylthiomethyl, aminobutyl, (CBZ)aminobutyl, cyclohexylmethyl, benzyloxymethyl, methylsulfinylethyl, methylsulfinylmethyl, and hydroxymethyl;

$R_{2'}$ is hydrogen;

$R_4$ is optionally substituted methyl or optionally substituted phenyl;

$R_6$ is tolyl, halophenyl, methylhalophenyl, hydroxymethylphenyl, halo(trifluoromethyl)phenyl-, methylenedioxyphenyl, formylphenyl or cyanophenyl; and $R_5$ is $R_{11}$-alkylene- wherein $R_1$ is amino, $C_1$-$C_4$ alkylamino-, di($C_1$-$C_4$ alkyl)amino-, $C_1$-$C_4$ alkoxy-, hydroxyl, or N-heterocyclyl.

5. The compound of claim 4 comprising one or more of the following:

$R_1$ is benzyl;

$R_{2'}$ is hydrogen;

$R_2$ is ethyl or propyl; and $R_5$ is aminoethyl, aminopropyl, aminobutyl, aminopentyl, aminohexyl, methylaminoethyl, methylaminopropyl, methylaminobutyl, methylaminopentyl, methylaminohexyl, dimethylaminoethyl, dimethylaminopropyl, dimethylaminobutyl, dimethylaminopentyl, dimethylaminohexyl, ethylaminoethyl, ethylaminopropyl, ethylaminobutyl, ethylaminopentyl, ethylaminohexyl, diethylaminoethyl, diethylaminopropyl, diethylaminobutyyl, diethylaminopentyl, or diethylaminohexyl.

6. The compound of claim 5 wherein $R_2$ is i-propyl.

7. The compound of claim 1 comprising one or more of the following:

T and T' are each a covalent bond;

$R_1$ is selected from hydrogen, optionally substituted $C_1$-$C_4$ alkyl, optionally substituted phenyl-$C_1$-$C_4$-alkyl-, optionally substituted naphthylmethyl, optionally substituted phenyl, and naphthyl $R_2$ is optionally substituted $C_1$-$C_4$ alkyl;

$R_{2'}$ is hydrogen or optionally substituted $C_1$-$C_4$ alkyl;

$R_4$ is hydrogen, halo, hydroxyl, optionally substituted lower alkyl, optionally substituted aryl, alkoxy, cyano, substituted amino, carbamyl, aryloxy, heteroaryloxy, heteroaryl; or optionally substituted N-heterocyclyl;

$R_6$ is selected from optionally substituted $C_1$-$C_8$ alkyl, optionally substituted aryl-$C_1$-$C_4$-alkyl-, optionally substituted heteroaryl-$C_1$-$C_4$-alkyl-, optionally substituted heteroaryl, optionally substituted aryl, $R_7$O— and $R_{12}$—NH—, $R_7$ is chosen from optionally substituted alkyl and optionally substituted aryl;

$R_{12}$ is chosen from optionally substituted alkyl and optionally substituted aryl; and R₃ taken together with R₅ and the nitrogen to which they are bound, forms an optionally substituted imidazolyl ring of the formula:

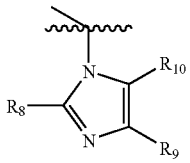

wherein
   R₈ is chosen from hydrogen, optionally substituted alkyl, optionally substituted aryl, optionally substituted aralkyl, optionally substituted heteroaralkyl, and optionally substituted heteroaryl; and
   R₉ and R₁₀ are independently hydrogen, optionally substituted alkyl, optionally substituted aryl, or optionally substituted aralkyl.

8. The compound of claim 7 comprising one or more of the following:
   R₁ is chosen from naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, chlorobenzyl, methylbenzyl, methoxybenzyl, cyanobenzyl, hydroxybenzyl, dichlorobenzyl, dimethoxybenzyl, or naphthylmethyl;
   R₂' is hydrogen;
   R₂ is optionally substituted C₁-C₄ alkyl;
   R₆ is chosen from phenyl; substituted phenyl; benzyl; phenoxymethyl-; halophenoxymethyl-; phenylvinyl-; heteroaryl-; substituted heteroaryl-; C₁-C₄ alkyl substituted with C₁-C₄ alkoxy-; and benzyloxymethyl-;
   R₄ is chosen from hydrogen, hydroxyl, halo, optionally substituted lower alkyl, lower alkoxy, optionally substituted phenyl, and cyano; and
   R₈ is aryl, substituted aryl, aralkyl, heteroaryl, substituted heteroaryl, heteroaralkyl, substituted aralkyl, or substituted heteroaralkyl.

9. The compound of claim 1 comprising one or more of the following:
   T and T' are each a covalent bond;
   R₁ is selected from hydrogen, optionally substituted C₁-C₄ alkyl, optionally substituted phenyl-C₁-C₄-alkyl-, optionally substituted naphthylmethyl, optionally substituted phenyl, and naphthyl;
   R₂ is optionally substituted C₁-C₄ alkyl;
   R₂' is hydrogen or optionally substituted C₁-C₄ alkyl;
   R₄ is hydrogen, halo, hydroxyl, optionally substituted lower alkyl, optionally substituted aryl, alkoxy, cyano, substituted amino, carbamyl, aryloxy, heteroaryloxy, heteroaryl, or optionally substituted N-heterocyclyl;
   R₆ is selected from optionally substituted C₁-C₈ alkyl, optionally substituted aryl-C₁-C₄-alkyl-, optionally substituted heteroaryl-C₁-C₄-alkyl-, optionally substituted heteroaryl, optionally substituted aryl, R₇O— and R₁₂—NH—,
   R₇ is chosen from optionally substituted alkyl and optionally substituted aryl;
   R₁₂ is chosen from optionally substituted alkyl and optionally substituted aryl; and R₃ taken together with R₅ and the nitrogen to which they are bound, forms an optionally substituted imidazolinyl ring of the formula:

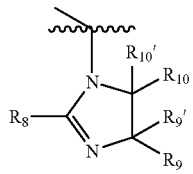

wherein,
   R₈ is chosen from hydrogen, optionally substituted alkyl, optionally substituted aryl, optionally substituted aralkyl, optionally substituted heteroaralkyl, and optionally substituted heteroaryl; and
   R₉, R₉', R₁₀, and R₁₀' are independently chosen from hydrogen, optionally substituted alkyl, optionally substituted aryl, and optionally substituted aralkyl.

10. The compound of claim 9 comprising one or more of the following:
   R₁ is chosen from naphthyl, phenyl, bromophenyl, chlorophenyl, methoxyphenyl, ethoxyphenyl, tolyl, dimethylphenyl, chorofluorophenyl, methylchlorophenyl, ethylphenyl, phenethyl, benzyl, chlorobenzyl, methylbenzyl, methoxybenzyl, cyanobenzyl, hydroxybenzyl, dichlorobenzyl, dimethoxybenzyl, or naphthylmethyl;
   R₂' is hydrogen;
   R₂ is optionally substituted C₁-C₄ alkyl;
   R₆ is chosen from phenyl; substituted phenyl; benzyl; phenoxymethyl-; halophenoxymethyl-; phenylvinyl-; heteroaryl-; substituted heteroaryl-; C₁-C₄ alkyl substituted with C₁-C₄ alkoxy-; and benzyloxymethyl-;
   R₄ is chosen from hydrogen, hydroxyl, halo, optionally substituted lower alkyl, lower alkoxy, optionally substituted phenyl, and cyano;
   R₈ is aryl, substituted aryl, aralkyl, heteroaryl, substituted heteroaryl, heteroaralkyl, substituted aralkyl, or substituted heteroaralkyl; and
   R₉, R₉', R₁₀, and R₁₀' are independently selected from the group consisting of hydrogen and optionally substituted lower alkyl.

11. The compound of claim 1 wherein
   T and T' are absent;
   R₁ is benzyl, halobenzyl, methylbenzyl, methoxylbenzyl, cyanobenzyl, hydroxybenzyl, or naphthylmethyl;
   R₂ is optionally substituted C₁-C₄ alkyl;
   R₂' is hydrogen;
   R₄ is optionally substituted methyl or optionally substituted phenyl;
   R₃ is hydrogen; and
   R₅ is hydrogen.

12. The compound of claim 1 wherein
   T and T' are absent;
   R₁ is benzyl, halobenzyl, methylbenzyl, methoxylbenzyl, cyanobenzyl, hydroxybenzyl, or naphthylmethyl;
   R₂ is optionally substituted C₁-C₄ alkyl;
   R₂' is hydrogen;
   R₄ is optionally substituted methyl or optionally substituted phenyl;
   R₃ is —C(O)R₆;
   R₆ is optionally substituted phenyl; and
   R₅ is optionally substituted alkyl.

13. The compound of claim 1 wherein
T and T' are absent;
$R_1$ is benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl;
$R_3$ is optionally substituted phenyl, heterocyclyl, or naphthyl; and
$R_5$ is optionally substituted alkyl.

14. The compound of claim 1 wherein
T and T' are absent;
$R_1$ is benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl; and
$R_3$ and $R_5$ taken together form an optionally substituted imidazolinyl ring.

15. The compound of claim 1 wherein
T and T' are absent;
$R_1$ is benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl; and
$R_3$ taken together with $R_5$ form an optionally substituted imidazolyl ring.

16. The compound of claim 1 wherein
T and T' are absent;
$R_1$ is benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl; and
$R_3$ and $R_5$ taken together form an optionally substituted imidazolidinyl ring.

17. The compound of claim 1 wherein
T and T' are absent;
$R_1$ is benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl; and
$R_3$ and $R_5$ taken together form an optionally substituted piperazinyl ring.

18. The compound of claim 1 wherein
T and T' are absent;
$R_1$ is benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl; and
$R_3$ and $R_5$ taken together form an optionally substituted diazepinoyl ring.

19. The compound of claim 1 wherein
T and T' are absent;
$R_1$ is most preferably chosen from benzyl, halobenzyl, methylbenzyl, methoxylbenzyl, cyanobenzyl, hydroxybenzyl, or naphthylmethyl;
$R_2$ is optionally substituted $C_1$-$C_4$ alkyl;
$R_{2'}$ is hydrogen;
$R_4$ is optionally substituted methyl or optionally substituted phenyl;
$R_5$ is optionally substituted alkyl;
$R_3$ is —$SO_2R_{6a}$, and
$R_{6a}$ is substituted phenyl or naphthyl.

20. The compound of claim 1 wherein the stereogenic center to which $R_2$ and $R_{2'}$ is attached is of the R configuration.

21. A pharmaceutical composition comprising a pharmaceutical excipient and a therapeutically effective amount of a compound of claim 1.

22. A method of treatment comprising administering an effective amount of a compound of claim 1 to a patient suffering from breast cancer.

23. A kit comprising a compound of claim 1 and a package insert or other labeling including directions for treating breast cancer by administering an effective amount of said compound.

* * * * *